(12) United States Patent
Igarashi et al.

(10) Patent No.: US 7,733,012 B2
(45) Date of Patent: Jun. 8, 2010

(54) LIGHT-EMITTING DEVICE AND AROMATIC COMPOUND

(75) Inventors: Tatsuya Igarashi, Minami-Ashigara (JP); Xuepeng Qui, Changchun (CN)

(73) Assignee: FUJIFILM Corporation, Tokyo (JP)

( * ) Notice: Subject to any disclaimer, the term of this patent is extended or adjusted under 35 U.S.C. 154(b) by 7 days.

(21) Appl. No.: 12/034,833

(22) Filed: Feb. 21, 2008

(65) Prior Publication Data

US 2008/0152948 A1 Jun. 26, 2008

Related U.S. Application Data

(62) Division of application No. 10/483,391, filed as application No. PCT/JP02/06998 on Jul. 10, 2002.

(30) Foreign Application Priority Data

Jul. 11, 2001 (JP) ............... 2001-211269
Oct. 26, 2001 (JP) ............... 2001-329676

(51) Int. Cl.
*C09K 11/06* (2006.01)
*H01L 51/54* (2006.01)
*H05B 33/14* (2006.01)
*C07C 13/465* (2006.01)

(52) U.S. Cl. .................. 313/504; 313/506; 257/40; 257/E51.026; 257/E51.049; 428/690; 428/917; 585/27

(58) Field of Classification Search ............... None
See application file for complete search history.

(56) References Cited

U.S. PATENT DOCUMENTS

| | | | |
|---|---|---|---|
| 5,077,142 A | 12/1991 | Sakon et al. | |
| 5,635,308 A * | 6/1997 | Inoue et al. | ........... 428/696 |
| 5,989,737 A | 11/1999 | Xie et al. | |
| 6,194,090 B1 | 2/2001 | Okada | |
| 6,461,747 B1 | 10/2002 | Okada et al. | |
| 6,635,364 B1 | 10/2003 | Igarashi | |
| 6,830,829 B2 | 12/2004 | Suzuki et al. | |
| 7,053,255 B2 * | 5/2006 | Ikeda et al. | ........... 585/26 |

FOREIGN PATENT DOCUMENTS

| | | |
|---|---|---|
| EP | 1 009 041 A2 | 6/2000 |
| EP | 1 009 043 A2 | 6/2000 |
| EP | 1 013 740 A2 | 6/2000 |
| JP | 04-068076 A | 3/1992 |
| JP | 2001-192651 A | 7/2001 |
| JP | 2001-335516 A | 12/2001 |

OTHER PUBLICATIONS

Ried et al., Chemische Berichte, (1960), vol. 93, pp. 1769-1773.*
Debad, et al., "Electrogenerated Chemiluminescence 60. Spectroscopic Properties and Electrogenerated Chemiluminescence of Decaphenylanthracene and Octaphenylnaphthalene," *Acta Chemica Scandanavia* 52:45-50 (1998).
Z.D. Popovic, et al., "Life Extension of Organic LED's by Doping of a Hole Transport Layer," *Thin Solid Films* 363:6-8 (2000).

* cited by examiner

*Primary Examiner*—D. Lawrence Tarazano
*Assistant Examiner*—Brett A Crouse
(74) *Attorney, Agent, or Firm*—Sughrue Mion, PLLC

(57) ABSTRACT

A light-emitting device comprising a pair of electrodes and a light-emitting layer or a plurality of organic layers comprising a light-emitting layer disposed therebetween, the light-emitting layer or at least one of a plurality of organic layers comprising the light-emitting layer comprising at least one compound represented by the following general formula (1): wherein each of $Ar^{11}$, $Ar^{12}$, $Ar^{13}$, $Ar^{14}$ and $Ar^{15}$ represents an aryl group or a heteroaryl group; Ar represents a benzene ring, a naphthalene ring, a phenanthrene ring or an anthracene ring; at least one of Ar, $Ar^{11}$, $Ar^{12}$, $Ar^{13}$, $Ar^{14}$ and $Ar^{15}$ is a condensed aryl group, a condensed or uncondensed heteroaryl group or a group comprising a condensed aryl group or a condensed or uncondensed heteroaryl group; $Ar^{11}$, $Ar^{12}$, $Ar^{13}$, $Ar^{14}$ and $Ar^{15}$ are not bonded to each other to form a ring; $R^{11}$ represents a substituent; and $n^{11}$ represents an integer of 0 or more.

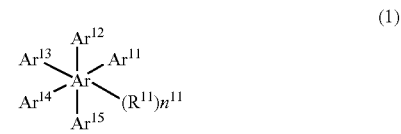

(1)

5 Claims, No Drawings

LIGHT-EMITTING DEVICE AND AROMATIC COMPOUND

FIELD OF THE INVENTION

The present invention relates to a light-emitting device that converts electric energy to light, particularly to a light-emitting device suitable for indicating elements, displays, backlights, electrophotography, illumination light sources, recording light sources, exposing light sources, reading light sources, signs and marks, signboards, interiors, optical communications devices, etc., and a novel aromatic compound usable for such a light-emitting device.

BACKGROUND OF THE INVENTION

Various display devices have been actively researched and developed in recent years. In particular, organic electroluminescence (EL) devices attract much attention because they can emit light at a high luminance with low voltage applied. For example, a light-emitting device comprising organic thin layers provided by vapor-depositing organic compounds is disclosed in Applied Physics Letters, Vol. 51, page 913 (1987). This light-emitting device has a structure where an electron-transporting material of tris(8-hydroxyquinolinato) aluminum complex (Alq) and a hole-transporting material of an amine compound are disposed between electrodes as a laminate, thereby exhibiting more excellent light-emitting properties than those of conventional light-emitting devices having a single-layer structure.

Active research and development have been made to apply organic EL devices to fill-color displays in recent years. To provide high-performance, full-color displays, light-emitting properties should be improved for each of blue, green and red colors. For instance, blue-color, light-emitting devices are disadvantageous in color purity, durability, light-emitting luminance and light-emitting efficiency, and thus their improvement is desired. To solve these problems, devices comprising aromatic condensed-ring compounds were investigated (JP 11-12205 A, etc.), but there is still a problem that such light-emitting devices are low in light-emitting efficiency, failing to emit blue light with high color purity. In addition, improvement is desired in organic EL devices, too.

OBJECT OF THE INVENTION

An object of the present invention is to provide a light-emitting device excellent in light-emitting properties and durability.

Another object of the present invention is to provide an aromatic compound excellent in color purity and durability, and usable for such light-emitting devices.

DISCLOSURE OF THE INVENTION

As a result of intense research in view of the above objects, the inventors have found that a light-emitting device comprising an aromatic compound having a particular structure is excellent in light-emitting properties and durability. The present invention has been completed based on this finding.

Thus, the light-emitting device of the present invention comprises a pair of electrodes and a light-emitting layer or a plurality of organic layers comprising a light-emitting layer disposed between the electrodes, either of the light-emitting layer or at least one of a plurality of organic layers comprising a light-emitting layer comprising at least one compound represented by the general formula (1):

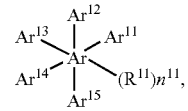

wherein each of $Ar^{11}$, $Ar^{12}$, $Ar^{13}$, $Ar^{14}$ and $Ar^{15}$ represents an aryl group or a heteroaryl group; Ar represents a benzene ring, a naphthalene ring, a phenanthrene ring or an anthracene ring; at least one of Ar, $Ar^{11}$, $Ar^{12}$, $Ar^{13}$, $Ar^{14}$ and $Ar^{15}$ is a condensed aryl group, a condensed or uncondensed heteroaryl group or a group comprising a condensed aryl group or a condensed or uncondensed heteroaryl group; $Ar^{11}$, $Ar^{12}$, $Ar^{13}$, $Ar^{14}$ and $Ar^{15}$ are not bonded to each other to form a ring; $R^{11}$ represents a substituent; and $n^{11}$ represents an integer of 0 or more.

In the general formula (1), at least one of $Ar^{11}$, $Ar^{12}$, $Ar^{13}$, $Ar^{14}$ and $Ar^{15}$ is a pyrenyl group.

In the above general formula (1), at least four of $R^{11}$, $Ar^{11}$, $Ar^{12}$, $Ar^{13}$, $Ar^{14}$ and $Ar^{15}$ are preferably a condensed aryl group or a condensed or uncondensed heteroaryl group, more preferably a condensed aryl group, most preferably a phenanthryl group or a pyrenyl group.

In the above general formula (1), at least one of $R^{11}$, $Ar^{11}$, $Ar^{12}$, $Ar^{13}$, $Ar^{14}$ and $Ar^{15}$ is selected from the group consisting of a naphthyl group, a phenanthryl group, an anthryl group, a fluoranthenyl group, a pyrenyl group and a perylenyl group, more preferably a naphthyl group or a phenanthryl group.

The compound represented by the general formula (1) preferably emits light from a singlet excited state.

The first preferred example of the general formula (1) is the following general formula (2):

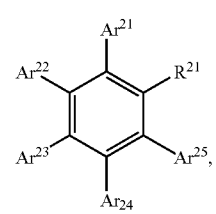

wherein each of $Ar^{21}$, $Ar^{22}$, $Ar^{23}$, $Ar^{24}$ and $Ar^{25}$ represents an aryl group or a heteroaryl group; at least one of $Ar^{21}$, $Ar^{22}$, $Ar^{24}$ and $Ar^{25}$ is a condensed aryl group, a condensed or uncondensed heteroaryl group or a group comprising a condensed aryl group or a condensed or uncondensed heteroaryl group; $Ar^{21}$, $Ar^{22}$, $Ar^{23}$, $Ar^{24}$ and $Ar^{25}$ are not bonded to each other to form a ring; $R^{21}$ represents a hydrogen atom or a substituent.

In the general formula (2), it is preferable that each of $Ar^{21}$, $Ar^{22}$, $Ar^{23}$ and $Ar^{24}$ is selected from the group consisting of a phenyl group, a naphthyl group, an anthryl group, a phenanthryl group and a fluoranthenyl group; $Ar^{25}$ is selected from the group consisting of a phenyl group, a naphthyl group, an anthryl group, a phenanthryl group, a fluoranthenyl group, a pyrenyl group and a perylenyl group; $R^{21}$ is selected from the group consisting of a hydrogen atom, an alkyl group and an aryl group; at least one of $Ar^{21}$, $Ar^{22}$, $Ar^{23}$, $Ar^{24}$ and $Ar^{25}$ is a condensed aryl group; $Ar^{21}$, $Ar^{22}$, $Ar^{23}$, $Ar^{24}$ and $Ar^{25}$ are not bonded to each other to form a ring.

In the general formula (2), each of $Ar^{21}$, $Ar^{22}$, $Ar^{23}$ and $Ar^{24}$ is more preferably selected from the group consisting of a phenyl group, a naphthyl group and a phenanthryl group, most preferably a phenyl group.

In the general formula (2), $Ar^{25}$ is more preferably selected from the group consisting of an anthryl group, a phenanthryl group, a fluoranthenyl group, a pyrenyl group and a perylenyl group.

In the general formula (2), $R^{21}$ is more preferably selected from the group consisting of a hydrogen atom, a phenyl group and a pyrenyl group.

In the above general formula (2), at least four of $R^{21}$, $Ar^{21}$, $Ar^{22}$, $Ar^{23}$, $Ar^{24}$ and $Ar^{25}$ are preferably a condensed aryl group or a condensed or uncondensed heteroaryl group, more preferably a condensed aryl group, most preferably a phenanthryl group or a pyrenyl group.

In the above general formula (2), each of $Ar^{21}$ and $Ar^{22}$ is a condensed aryl group or a condensed or uncondensed heteroaryl group, more preferably a condensed aryl group, most preferably a phenanthryl group or a pyrenyl group.

In the above general formula (2), each of $Ar^{21}$ and $Ar^{24}$ is preferably a condensed aryl group or a condensed or uncondensed heteroaryl group, more preferably a condensed aryl group, most preferably a phenanthryl group or a pyrenyl group.

In the above general formula (2), at least one of $R^{11}$, $Ar^{11}$, $Ar^{12}$, $Ar^{13}$, $Ar^{14}$ and $Ar^{15}$ is selected from the group consisting of a naphthyl group, a phenanthryl group, an anthryl group, a fluoranthenyl group, a pyrenyl group and a perylenyl group, more preferably a naphthyl group or a phenanthryl group.

In the above general formula (2), it is preferable that each of $Ar^{21}$ and $Ar^{23}$ is a condensed aryl group, and that each of $R^{21}$, $Ar^{22}$, $Ar^{24}$ and $Ar^{25}$ is selected from the group consisting of a phenyl group, a naphthyl group, a phenanthryl group, an anthryl group, a fluoranthenyl group, a pyrenyl group and a perylenyl group; and it is more preferable that each of $Ar^{21}$ and $Ar^{23}$ is a pyrenyl group, and that each of $R^{21}$, $Ar^{22}$, $Ar^{24}$ and $Ar^{25}$ is selected from the group consisting of a phenyl group, a naphthyl group and a phenanthryl group.

The first preferred example of the general formula (2) is the following general formula (5):

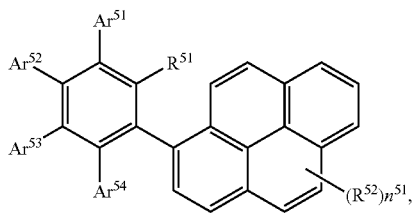

(5)

wherein each of $Ar^{51}$, $Ar^{52}$, $Ar^{53}$ and $Ar^{54}$ represents an aryl group, $R^{51}$ represents a hydrogen atom or a substituent, $R^{52}$ represents a substituent, and $n^{51}$ is an integer of 0 to 9.

In the general formula (5), each of $Ar^{51}$, $Ar^{52}$, $Ar^{53}$ and $Ar^{54}$ is preferably selected from the group consisting of a phenyl group, a naphthyl group, an anthryl group, a phenanthryl group and a fluoranthenyl group, more preferably a phenyl group.

In the general formula (5), $R^{51}$ is preferably selected from the group consisting of a hydrogen atom, an alkyl group and an aryl group, more preferably selected from the group consisting of a hydrogen atom, a phenyl group and a pyrenyl group, most preferably a phenyl group or a pyrenyl group.

The second preferred example of the general formula (2) is the following general formula (6):

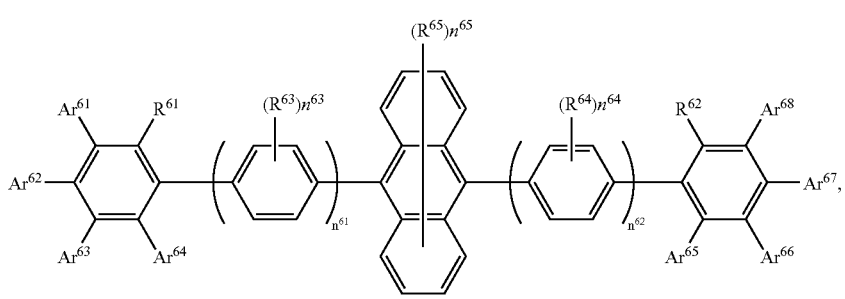

(6)

wherein each of $Ar^{61}$, $Ar^{62}$, $Ar^{63}$, $Ar^{64}$, $Ar^{65}$, $Ar^{66}$, $Ar^{67}$ and $Ar^{68}$ represents an aryl group or a heteroaryl group; each of $R^{61}$ and $R^{62}$ represents a hydrogen atom or a substituent; each of $R^{63}$, $R^{64}$ and $R^{65}$ represents a substituent; each of $n^{61}$ and $n^{62}$ is an integer of 0 to 5; each of $n^{63}$ and $n^{64}$ is an integer of 0 to 4; and $n^{65}$ is an integer of 0 to 8.

In the general formula (6), each of $Ar^{61}$, $Ar^{62}$, $Ar^{63}$, $Ar^{64}$, $Ar^{65}$, $Ar^{66}$, $Ar^{67}$ and $Ar^{68}$ is preferably selected from the group consisting of a phenyl group, a naphthyl group and a phenanthryl group. In particular, each of $R^{61}$ and $R^{62}$ is preferably selected from the group consisting of a hydrogen atom, a phenyl group and a pyrenyl group. Each of $n^{61}$ and $n^{62}$ is preferably 0 or 1.

The second preferred example of the general formula (1) is the following general formula (3):

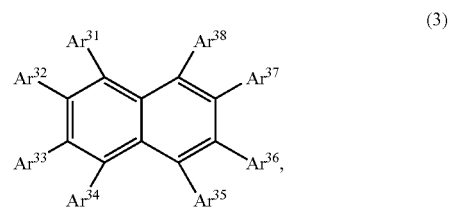

(3)

wherein each of $Ar^{31}$, $Ar^{32}$, $Ar^{33}$, $Ar^{34}$, $Ar^{35}$, $Ar^{36}$, $Ar^{37}$ and $Ar^{38}$ represents an aryl group or a heteroaryl group; and $Ar^{31}$, $Ar^{32}$, $Ar^{33}$, $Ar^{34}$, $Ar^{35}$, $Ar^{36}$, $Ar^{37}$ and $Ar^{38}$ are not bonded to each other to form a ring.

In the general formula (3), each of $Ar^{31}$, $Ar^{32}$, $Ar^{33}$, $Ar^{34}$, $Ar^{35}$, $Ar^{36}$, $Ar^{37}$ and $Ar^{38}$ is preferably an aryl group, more preferably selected from the group consisting of a phenyl group, a naphthyl group, an anthryl group, a phenanthryl group and a pyrenyl group, most preferably a phenyl group.

The third preferred example of the general formula (1) is the following general formula (4):

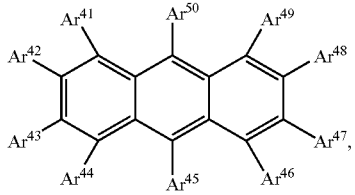

(4)

wherein each of $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ represents an aryl group or a heteroaryl group; and $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ are not bonded to each other to form a ring.

In the general formula (4), each of $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ is preferably an aryl group, more preferably selected from the group consisting of a phenyl group, a naphthyl group, an anthryl group, a phenanthryl group and a pyrenyl group, most preferably a phenyl group.

The compound of the general formula (1) is preferably represented by any one of the above general formulae (2)-(4), more preferably represented by the general formula (2).

The content of the compound represented by the general formula (1) in the light-emitting layer is preferably 0.1 to 100% by mass as a light-emitting material.

The content of the compound represented by the general formula (1) in the light-emitting layer or at least one of a plurality of organic layers comprising the light-emitting layer is preferably 10 to 99.9% by mass as a host material.

At least one of the above light-emitting layer and a plurality of organic layers comprising the above light-emitting layer is preferably a light-emitting layer.

At least one of the above light-emitting layer and a plurality of organic layers comprising the above light-emitting layer is preferably a hole-transporting layer.

The above light-emitting layer preferably comprises at least one fluorescent compound.

The aromatic compound of the present invention is represented by the general formula (5):

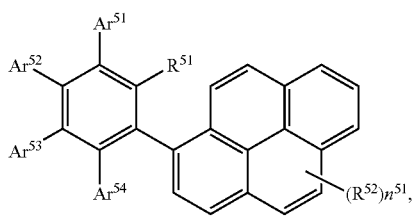

(5)

wherein each of $Ar^{51}$, $Ar^{52}$, $Ar^{53}$ and $Ar^{54}$ represents an aryl group; $R^{51}$ represents a hydrogen atom or a substituent; $R^{52}$ represents a substituent; and $n^{51}$ is an integer of 0 to 9.

In the general formula (5), each of $Ar^{51}$, $Ar^{52}$, $Ar^{53}$ and $Ar^{54}$ is preferably selected from the group consisting of a phenyl group, a naphthyl group, an anthryl group, a phenanthryl group and a fluoranthenyl group, more preferably a phenyl group.

In the general formula (5), $R^{51}$ is preferably selected from the group consisting of a hydrogen atom, an alkyl group and an aryl group, more preferably selected from the group consisting of a hydrogen atom, a phenyl group and a pyrenyl group, most preferably a phenyl group or a pyrenyl group.

The aromatic compound represented by the general formula (5) is a preferred example of the compound represented by the general formula (2), which can preferably be used as the compound represented by the general formula (1).

BEST MODE FOR CARRYING OUT THE INVENTION

The light-emitting device of the present invention comprises a pair of electrodes and a light-emitting layer and a plurality of organic layers comprising a light-emitting layer disposed therebetween. The light-emitting layer or at least one layer in a plurality of organic layers comprising the light-emitting layer comprises at least one compound represented by the following general formula (1). The compound represented by any one of the general formulae (1)-(6) may be referred to as "compound (1)" or "compound of the present invention" hereinafter.

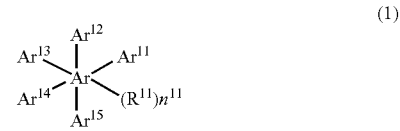

(1)

In the general formula (1), each of $Ar^{11}$, $Ar^{12}$, $Ar^{13}$, $Ar^{14}$ and $Ar^{15}$ represents an aryl group or a heteroaryl group. Examples of the aryl groups include a phenyl group, a naphthyl group, an anthryl group, a phenanthryl group, a fluoranthenyl group, a pyrenyl group, a perylenyl group, a chrysenyl group, a triphenylenyl group, a benzoanthryl group, a benzophenanthryl group, etc. Preferable among them are a phenyl group, a naphthyl group, an anthryl group, a phenanthryl group, a pyrenyl group and a perylenyl group. Examples of the condensed or uncondensed heteroaryl groups include a pyridyl group, a quinolyl group, a quinoxalyl group, a quinazolyl group, an acridyl group, a phenanthridyl group, a phthalazyl group, a phenanthrolyl group, a triazyl group, etc. Preferable among them are a pyridyl group, a quinolyl group and a triazyl group. Each of $Ar^{11}$, $Ar^{12}$, $Ar^{13}$, $Ar^{14}$ and $Ar^{15}$ may have a substituent, whose examples may be the same as those of $R^{11}$ described later. Each of $Ar^{11}$, $Ar^{12}$, $Ar^{13}$, $Ar^{14}$ and $Ar^{15}$ is preferably an aryl group. $Ar^{11}$, $Ar^{12}$, $Ar^{13}$, $Ar^{14}$ and $Ar^{15}$ are not bonded to each other to form a ring.

In the general formula (1), Ar represents a benzene ring, a naphthalene ring, a phenanthrene ring or an anthracene ring. Ar is preferably a benzene ring or a naphthalene ring, more preferably a benzene ring.

At least one of Ar, $Ar^{11}$, $Ar^{12}$, $Ar^{13}$, $Ar^{14}$ and $Ar^{15}$ is a condensed aryl group or a group comprising a condensed aryl group, such as a naphthyl group, a phenanthryl group, an anthryl group, a pyrenyl group, a perylenyl group, a fluoranthenyl group, etc.; or a condensed or uncondensed heteroaryl group or a group comprising a condensed or uncondensed heteroaryl group, such as a pyridyl group, a quinolyl group, a quinoxalyl group, a quinazolyl group, an acridyl group, a phenanthridyl group, a phthalazyl group, a phenanthrolyl group, a triazyl group, etc. At least one of Ar, $Ar^{11}$, $Ar^{12}$, $Ar^{13}$, $Ar^{14}$ and $Ar^{15}$ is preferably a condensed aryl group or a group comprising a condensed aryl group, more preferably a pyrenyl group. The number of pyrenyl groups m the compound (1) is preferably two or less. The above group comprising a condensed aryl group or a condensed or uncondensed heteroaryl group may be composed of a condensed aryl group or a condensed or uncondensed heteroaryl group, and an alkylene group, an arylene group, etc., though it is preferably composed of only a condensed aryl group or a condensed or uncondensed heteroaryl group.

In the general formula (1), $R^{11}$ represents a substituent. Examples of the substituents $R^{11}$ include alkyl groups, the number of carbon atoms thereof being preferably 1 to 30, more preferably 1 to 20, most preferably 1 to 10, such as a methyl group, an ethyl group, an isopropyl group, a t-butyl group, a n-octyl group, a n-decyl group, a n-hexadecyl group, a cyclopropyl group, a cyclopentyl group and a cyclohexyl group; alkenyl groups, the number of carbon atoms thereof being preferably 2 to 30, more preferably 2 to 20, most preferably 2 to 10, such as a vinyl group, an allyl group, a 2-butenyl group and a 3-pentenyl group; alkynyl groups, the number of carbon atoms thereof being preferably 2 to 30, more preferably 2 to 20, most preferably 2 to 10, such as a propargyl group and a 3-pentynyl group; aryl groups, the number of carbon atoms thereof being preferably 6 to 30, more preferably 6 to 20, most preferably 6 to 12, such as a phenyl group, a p-methylphenyl group, a naphthyl group and an anthranil group; amino groups, the number of carbon atoms thereof being preferably 0 to 30, more preferably 0 to 20, most preferably 0 to 10, such as an amino group, a methylamino group, a dimethylamino group, a diethylamino group, a dibenzylamino group, a diphenylamino group and a ditolylamino group; alkoxy groups, the number of carbon atoms thereof being preferably 1 to 30, more preferably 1 to 20, most preferably 1 to 10, such as a methoxy group, an ethoxy group, a butoxy group and a 2-ethylhexyloxy group; aryloxy groups, the number of carbon atoms thereof being preferably 6 to 30, more preferably 6 to 20, most preferably 6 to 12, such as a phenyloxy group, a 1-naphthyloxy group and a 2-naphthyloxy group; heterocyclicoxy groups, the number of carbon atoms thereof being preferably 1 to 30, more preferably 1 to 20, most preferably 1 to 12, such as a pyridyloxy group, a pyrazyloxy group, a pyrimidyloxy group and a quinolyloxy group; acyl groups, the number of carbon atoms thereof being preferably 1 to 30, more preferably 1 to 20, most preferably 1 to 12, such as an acetyl group, a benzoyl group, a formyl group and a pivaloyl group; alkoxycarbonyl groups, the number of carbon atoms thereof being preferably 2 to 30, more preferably 2 to 20, most preferably 2 to 12, such as a methoxycarbonyl group and an ethoxycarbonyl group; aryloxycarbonyl groups, the number of carbon atoms thereof being preferably 7 to 30, more preferably 7 to 20, most preferably 7 to 12, such as a phenyloxycarbonyl group; acyloxy groups, the number of carbon atoms thereof being preferably 2 to 30, more preferably 2 to 20, most preferably 2 to 10, such as an acetoxy group and a benzoyloxy group; acylamino groups, the number of carbon atoms thereof being preferably 2 to 30, more preferably 2 to 20, most preferably 2 to 10, such as an acetylamino group and a benzoylamino group; alkoxycarbonylamino groups, the number of carbon atoms thereof being preferably 2 to 30, more preferably 2 to 20, most preferably 2 to 12, such as a methoxycarbonylamino group; aryloxycarbonylamino groups, the number of carbon atoms thereof being preferably 7 to 30, more preferably 7 to 20, most preferably 7 to 12, such as a phenyloxycarbonylamino group; sulfonylamino groups, the number of carbon atoms thereof being preferably 1 to 30, more preferably 1 to 20, most preferably 1 to 12, such as a methanesulfonylamino group and a benzenesulfonylamino group; sulfamoyl groups, the number of carbon atoms thereof being preferably 0 to 30, more preferably 0 to 20, most preferably 0 to 12, such as a sulfamoyl group, a methylsulfamoyl group, a dimethylsulfamoyl group and a phenylsulfamoyl group; carbamoyl groups, the number of carbon atoms thereof being preferably 1 to 30, more preferably 1 to 20, most preferably 1 to 12, such as a carbamoyl group, a methylcarbamoyl group, a diethylcarbamoyl group, a phenylcarbamoyl group; alkylthio groups, the number of carbon atoms thereof being preferably 1 to 30, more preferably 1 to 20, most preferably 1 to 12, such as a methylthio group and an ethylthio group; arylthio groups, the number of carbon atoms thereof being preferably 6 to 30, more preferably 6 to 20, most preferably 6 to 12, such as a phenylthio group; heterocyclic thio groups, the number of carbon atoms thereof being preferably 1 to 30, more preferably 1 to 20, most preferably 1 to 12, such as a pyridylthio group, a 2-benzimidazolylthio group, a 2-benzoxazolylthio group and a 2-benzthiazolylthio group; sulfonyl groups, the number of carbon atoms thereof being preferably 1 to 30, more preferably 1 to 20, most preferably 1 to 12, such as a mesyl group and a tosyl group; sulfinyl groups, the number of carbon atoms thereof being preferably 1 to 30, more preferably 1 to 20, most preferably 1 to 12, such as a methane sulfinyl group and a benzene sulfinyl group; ureide groups, the number of carbon atoms thereof being preferably 1 to 30, more preferably 1 to 20, most preferably 1 to 12, such as a ureide group, a methylureide group and a phenylureide group; phosphoric amide groups, the number of carbon atoms thereof being preferably 1 to 30, more preferably 1 to 20, most preferably 1 to 12, such as a diethylphosphoric amide group and a phenylphosphoric amide group; a hydroxyl group; mercapto groups; halogen atoms such as a fluorine atom, a chlorine atom, a bromine atom and an iodine atom; cyano groups; sulfo groups; carboxyl groups; nitro groups; a hydroxamic acid group; a sulfino group; a hydrazino group; an imino group; heterocyclic groups that may have a nitrogen atom, a oxygen atom, a sulfur atom, etc. as a hetero atom, the number of carbon atoms thereof being preferably 1 to 30, more preferably 1 to 12, such as an imidazolyl group, a pyridyl group, a quinolyl group, a furyl group, a thienyl group, a piperidyl group, a morpholino group, a benzoxazolyl group, a benzimidazolyl group, a benzthiazolyl group, a carbazolyl group, an azepinyl group and a triazyl group; silyl groups, the number of carbon atoms thereof being preferably 3 to 40, more preferably 3 to 30, most preferably 3 to 24, such as a trimethylsilyl group and a triphenylsilyl group; siloxy groups, the number of carbon atoms thereof being preferably 3 to 30, more preferably 6 to 30, such as a triphenylsilyloxy group, a t-butyldimethylsilyloxy group; etc. These substituents may be further substituted. $R^{11}$ is preferably an alkyl group or an aryl group.

In the general formula (1), $n^{11}$ represents an integer of 0 or more, preferably 0 to 5, more preferably 0 to 2, most preferably 1.

From the viewpoint of vapor depositability during the production of the light-emitting device, the number of benzene rings in the compound (1) is preferably 15 or less. Also, when the compound (1) comprises a condensed group having four or more rings, such as a pyrene group, a triphenylene group, etc., the number of the condensed group having four or more rings is preferably 2 or less.

The compound (1) is represented preferably by the following general formula (2), (3) or (4), more preferably by the general formula (2), further preferably by the following general formula (5) or (6), most preferably by the general formula (5). The compound represented by the general formula (4) is preferably represented by the following general formula (6).

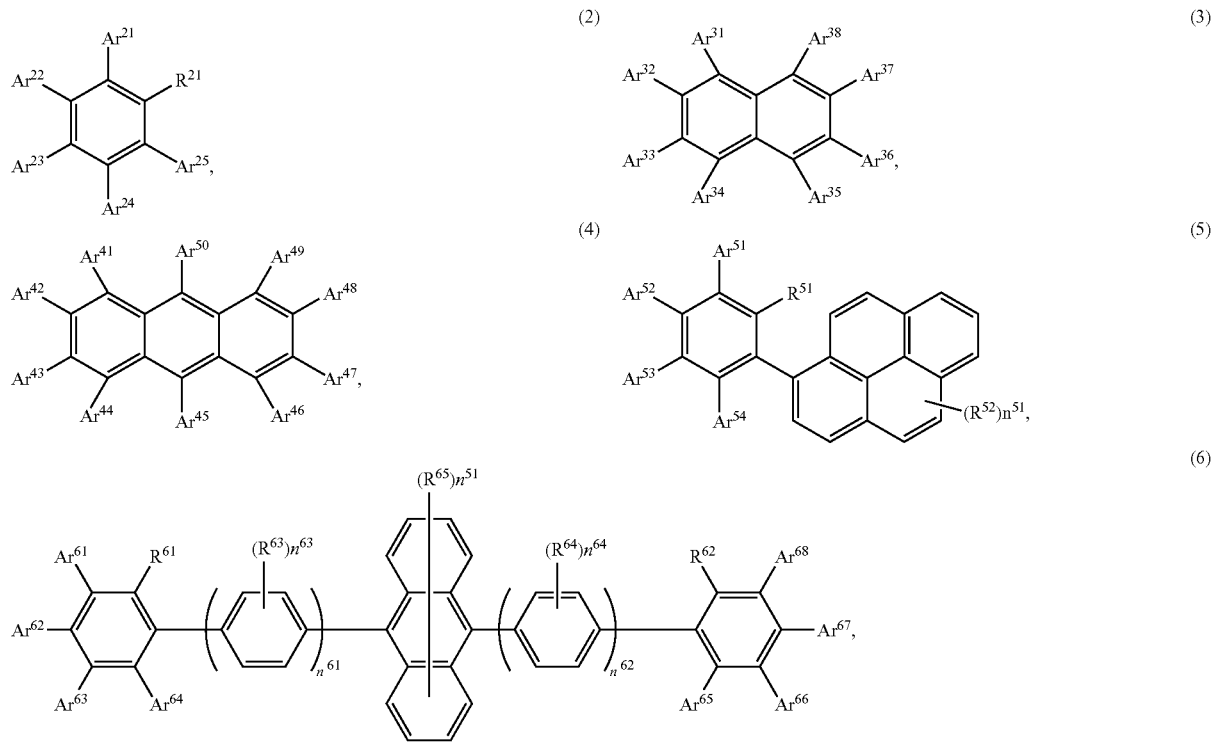

In the general formula (2), each of $Ar^{21}$, $Ar^{22}$, $Ar^{23}$, $Ar^{24}$ and $Ar^{25}$ represents an aryl group or a heteroaryl group, preferably an aryl group. Each of $Ar^{21}$, $Ar^{22}$, $Ar^{23}$, $Ar^{24}$ and $Ar^{25}$ may have a substituent. Examples of the substituents may be the same as those of $R^{11}$ described above. At least one of $Ar^{21}$, $Ar^{22}$, $Ar^{23}$, $Ar^{24}$ and $Ar^{25}$ is a condensed aryl group, a condensed or uncondensed heteroaryl group or a group comprising a condensed aryl group or a condensed or uncondensed heteroaryl group. Each of $Ar^{21}$, $Ar^{22}$, $Ar^{23}$ and $Ar^{24}$ is preferably a phenyl group, a naphthyl group, an anthryl group, a phenanthryl group or a fluoranthenyl group, more preferably a phenyl group, a naphthyl group, an anthryl group or a phenanthryl group, further preferably a phenyl group, a naphthyl group or a phenanthryl group, most preferably a phenyl group. $Ar^{25}$ is preferably a phenyl group, a naphthyl group, a phenanthryl group, an anthryl group, a pyrenyl group, a perylenyl group or a fluoranthenyl group, more preferably a phenanthryl group, an anthryl group or a pyrenyl group, most preferably a pyrenyl group. $Ar^{21}$, $Ar^{22}$, $Ar^{23}$, $Ar^{24}$ and $Ar^{25}$ are not bonded to each other to form a ring.

In the general formula (2), $R^{21}$ represents a hydrogen atom or a substituent. Examples of the substituents may be the same as those of $R^{11}$ described above. $R^{21}$ is preferably a hydrogen atom, an alkyl group or an aryl group, more preferably a hydrogen atom, a phenyl group or a pyrenyl group, most preferably a pyrenyl group.

In the general formula (3), each of $Ar^{31}$, $Ar^{32}$, $Ar^{33}$, $Ar^{34}$, $A^{35}$, $Ar^{36}$, $Ar^{37}$ and $Ar^{38}$ represents an aryl group or a heteroaryl group. Each of $Ar^{31}$, $Ar^{32}$, $Ar^{33}$, $Ar^{34}$, $Ar^{35}$, $Ar^{36}$, $Ar^{37}$ and $Ar^{38}$ may have a substituent, whose examples maybe the same as those of $R^{11}$ described above. $Ar^{31}$, $Ar^{32}$, $Ar^{33}$, $Ar^{34}$, $Ar^{35}$, $Ar^{36}$, $Ar^{37}$ and $Ar^{38}$ are not bonded to each other to form a ring. Each of $Ar^{31}$, $Ar^{32}$, $Ar^{33}$, $Ar^{34}$, $Ar^{35}$, $Ar^{36}$, $Ar^{37}$ and $Ar^{38}$ is preferably an aryl group, more preferably a phenyl group, a naphthyl group, an anthryl group, a pyrenyl group or a phenanthryl group, most preferably a phenyl group.

In the general formula (4), each of $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ represents an aryl group or a heteroaryl group. Each of $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ may have a substituent, whose examples may be the same as those of $R^{11}$ described above. $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ are not bonded to each other to form a ring. Each of $Ar^{41}$, $Ar^{42}$, $Ar^{43}$, $Ar^{44}$, $Ar^{45}$, $Ar^{46}$, $Ar^{47}$, $Ar^{48}$, $Ar^{49}$ and $Ar^{50}$ is preferably an aryl group, more preferably a phenyl group, a naphthyl group, an anthryl group, a pyrenyl group or a phenanthryl group, most preferably a phenyl group.

In the general formula (5), each of $Ar^{51}$, $Ar^{52}$, $Ar^{53}$ and $Ar^{54}$ represents an aryl group, preferably a phenyl group, a naphthyl group, an anthryl group, a phenanthryl group or a fluoranthenyl group, more preferably a phenyl group, a naphthyl group, an anthryl group or a phenanthryl group, further preferably a phenyl group, a naphthyl group or a phenanthryl group, most preferably a phenyl group. Each of $Ar^{51}$, $Ar^{52}$, $Ar^{53}$ and $Ar^{54}$ may have a substituent, whose examples may be the same as those of $R^{11}$ described above.

In the general formula (5), $R^{51}$ represents a hydrogen atom or a substituent. Examples of the substituents may be the same as those of $R^{11}$ described above. $R^{51}$ is preferably a hydrogen atom, an alkyl group or an aryl group, more preferably a hydrogen atom, a phenyl group or a pyrenyl group, most preferably a pyrenyl group.

In the general formula (5), $R^{52}$ represents a substituent, whose examples may be the same as those of $R^{11}$ described above. $R^{52}$ is preferably an alkyl group or an aryl group. $n^{51}$ represents the number of $R^{52}$, which is an integer of 0 to 9, preferably 0 to 2, more preferably 0. The number of pyrenyl groups in the compound represented by the general formula (5) is preferably two or less.

In the general formula (6), $Ar^{61}$ and $Ar^{68}$ are the same as the above $Ar^{21}$; $Ar^{62}$ and $Ar^{67}$ are the same as the above $Ar^{22}$; $Ar^{63}$ and $Ar^{66}$ are the same as the above $Ar^{23}$; and $Ar^{64}$ and $Ar^{65}$ are the same as the above $Ar^{24}$, in their definitions and preferred examples. Each of $Ar^{61}$, $Ar^{62}$, $Ar^{63}$, $Ar^{64}$, $Ar^{65}$, $Ar^{66}$, $Ar^{67}$ and $Ar^{68}$ may have a substituent, whose examples may be the same as those of $R^{11}$ described above. Each of $n^{61}$ and $n^{62}$ represents an integer of 0 to 5, preferably 0 to 3, more preferably 0 or 1.

In the general formula (6), $R^{61}$ and $R^{62}$ are the same as the above $R^{21}$ in their definitions and preferred examples. $R^{63}$, $R^{64}$ and $R^{65}$ are the same as the above $R^{52}$ in their definitions and preferred examples. Each of $n^{63}$ and $n^{64}$ represents an integer of 0 to 4, preferably 0 or 1, more preferably 0. $n^{65}$ represents an integer of 0 to 8, preferably 0 to 2, more preferably 0.

The compound (1) is preferably a low-molecular-weight compound and it may be an oligomer or a polymer. In a case where the compound (1) is a polymer or an oligomer, its weight-average molecular weight determined with polystyrene as a standard is preferably 1,000 to 5,000,000, more preferably 2,000 to 1,000,000, most preferably 3,000 to 100,000. The polymer may contain a moiety represented by the formula (1) in its main or side chain. The polymer may be a homopolymer or a copolymer.

The compound (1) preferably has the maximum emitting wavelength $\lambda_{max}$ of 370 to 500 nm in a fluorescence spectrum of its single layer or powder. $\lambda_{max}$ is more preferably 390 to 480 nm, further preferably 400 to 460 nm, and most preferably 400 to 440 nm.

Each of the compounds represented by the general formula (1), compounds used in the electron-transporting layer and compounds used in the hole-transporting layer has a glass transition temperature Tg of preferably 100° C. or higher, more preferably 120° C. or higher, further preferably 140° C. or higher, particularly preferably 160° C. or higher.

The light-emitting device of the present invention preferably further contains at least one fluorescent compound in its light-emitting layer. Within the preferred range of the fluorescent compounds are compounds described herein as materials for the light-emitting layer and their derivatives.

Specific examples of the compounds (1) are illustrated below without intention of restriction.

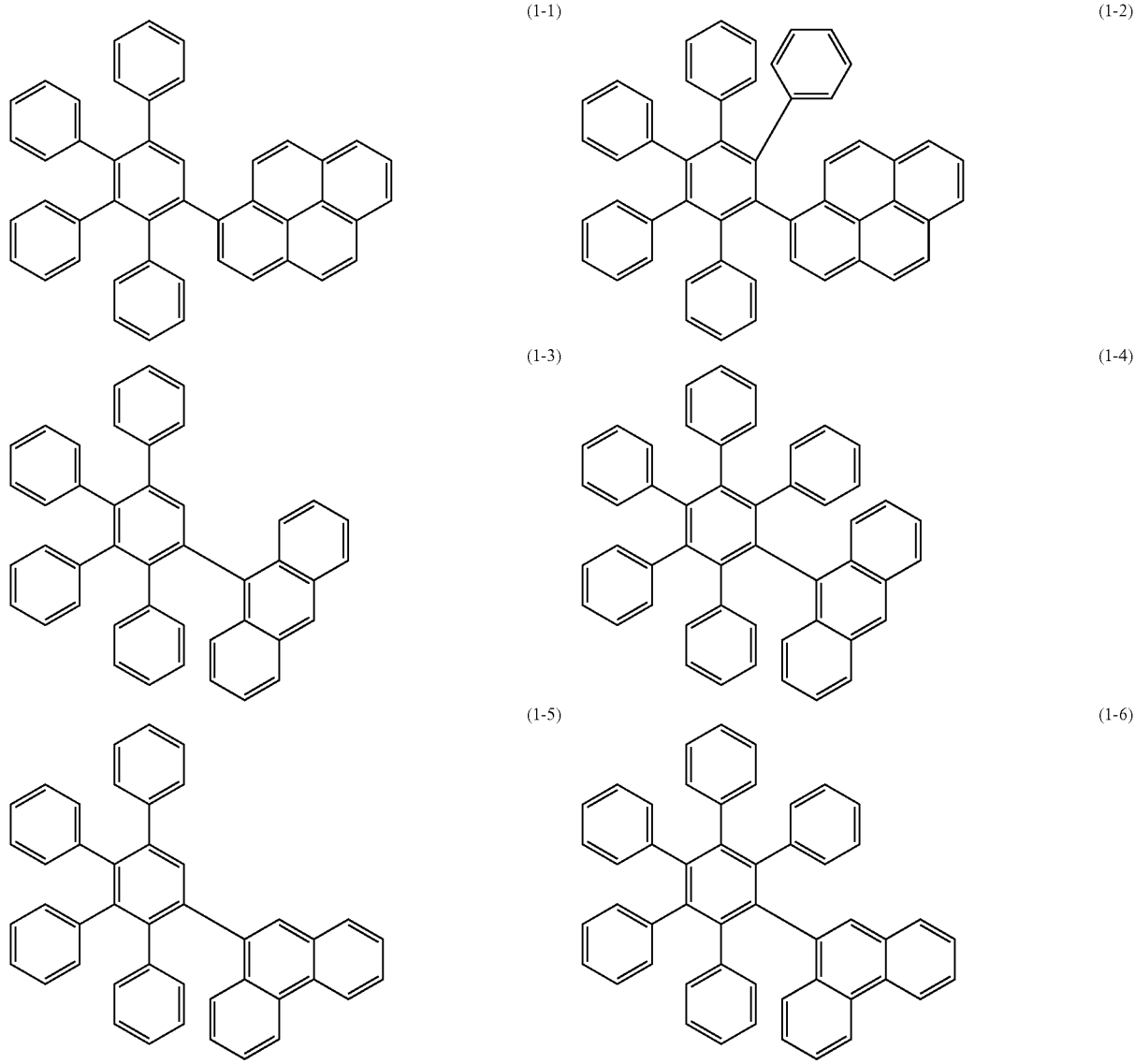

-continued
(1-7)
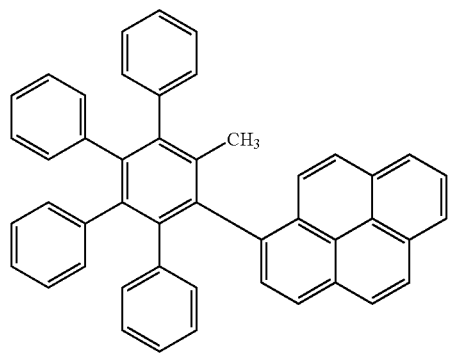
(1-8)
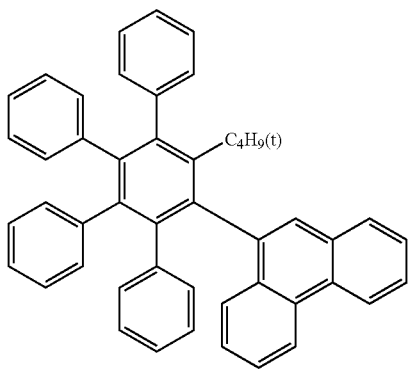
(1-9)
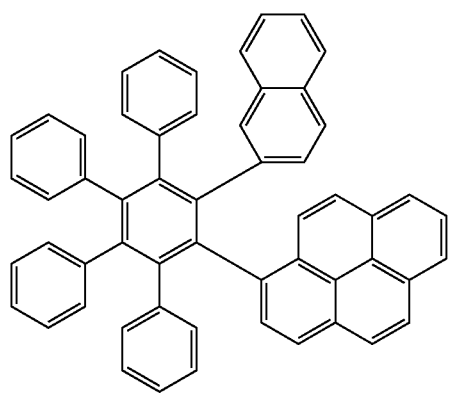
(1-10)
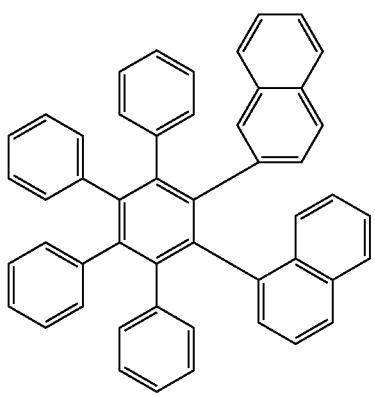
(1-11)
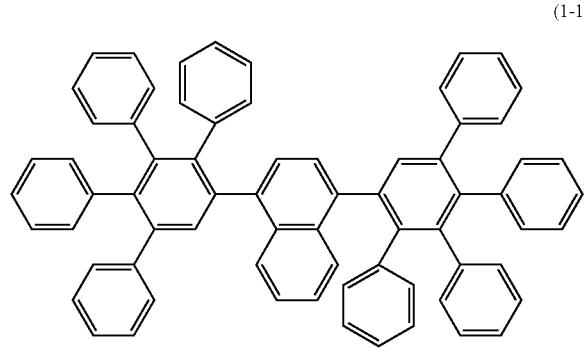
(1-12)
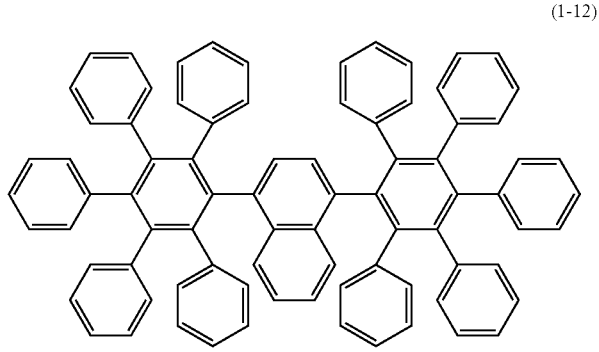
(1-13)
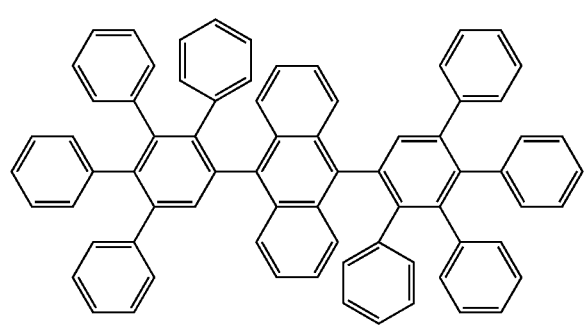
(1-14)
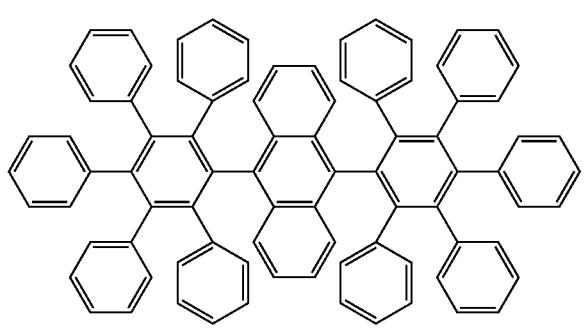

-continued
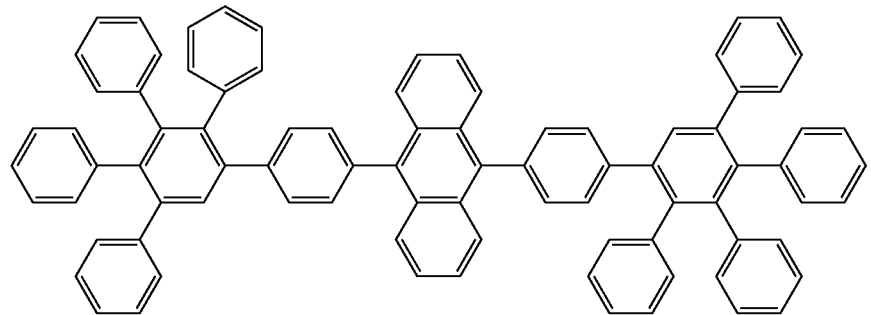
(1-15)
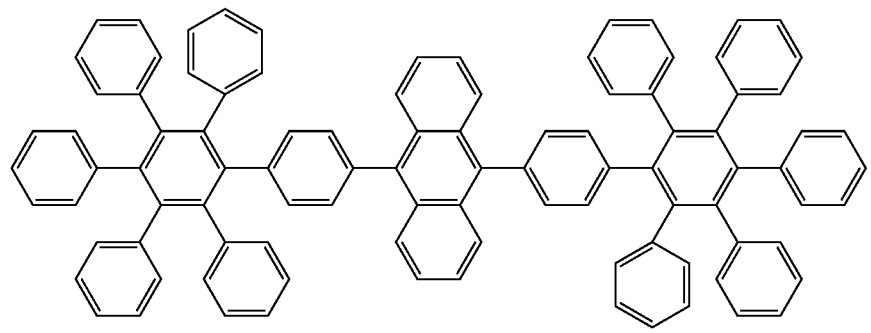
(1-16)
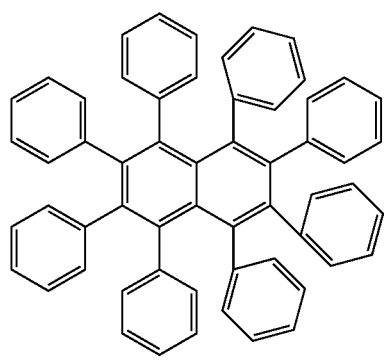
(1-17)
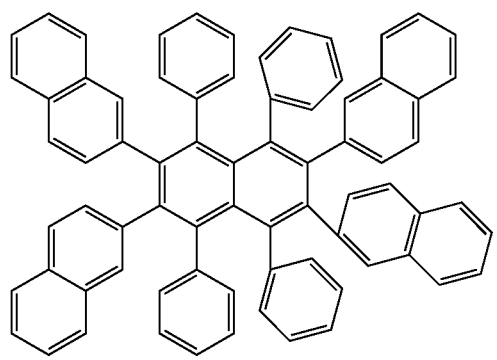
(1-18)
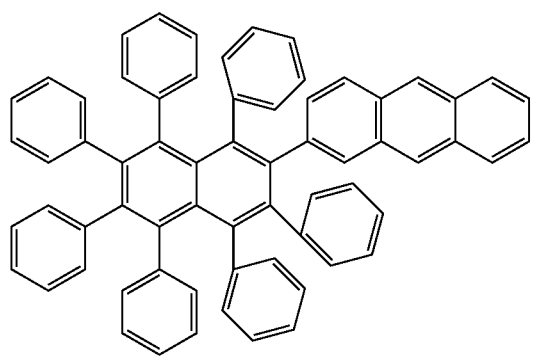
(1-19)
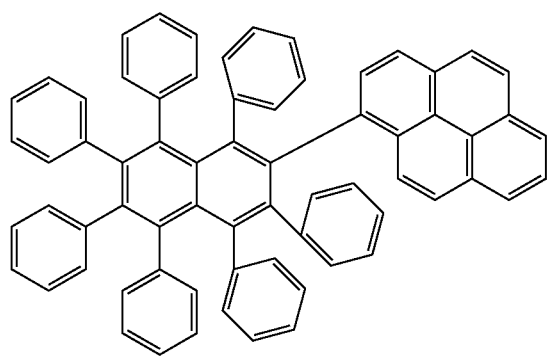
(1-20)

(1-21)
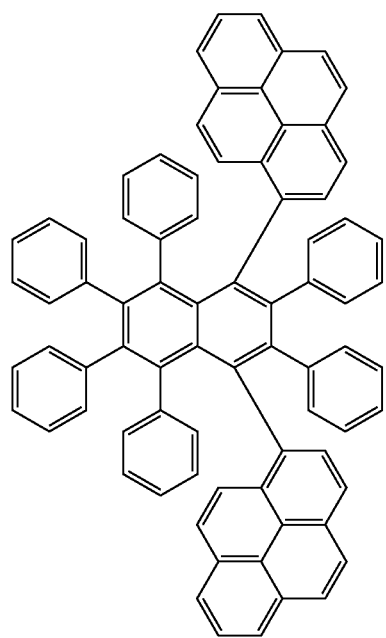
(1-22)
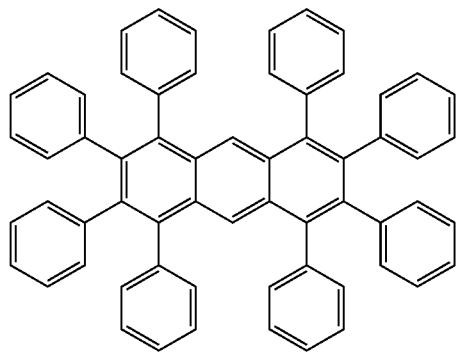
(1-23)
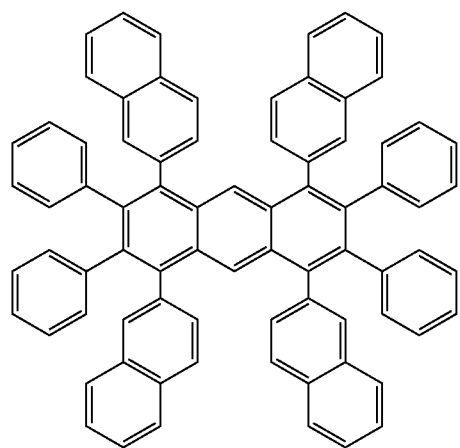
(1-24)
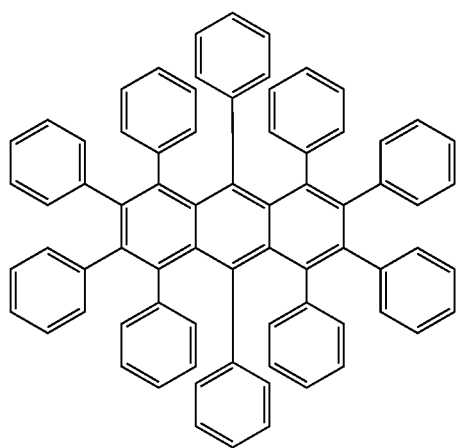
(1-25)
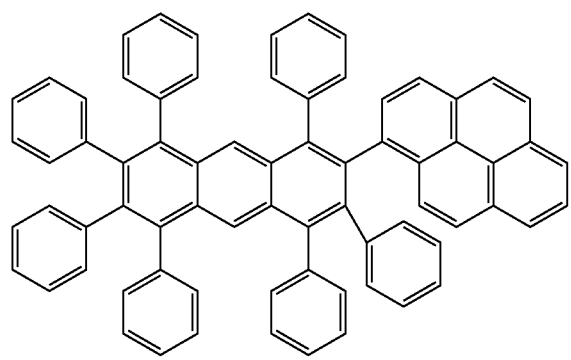
(1-26)
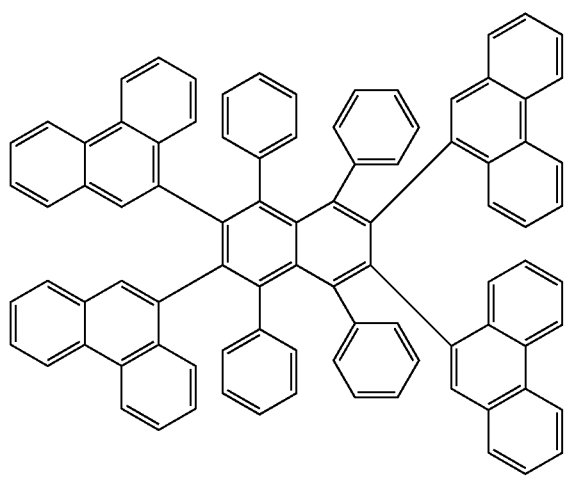

-continued
(1-27)
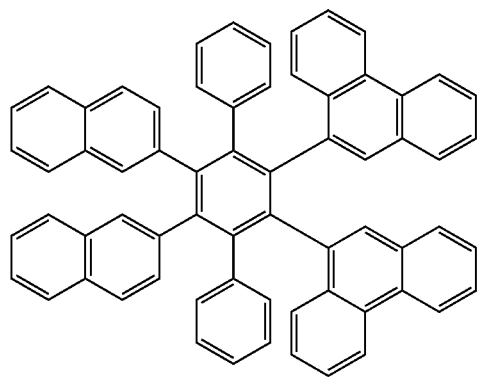
(1-28)
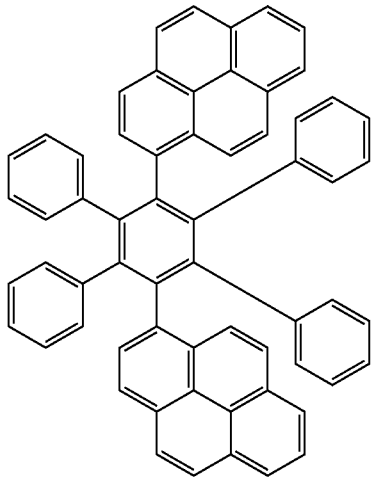
(1-29)
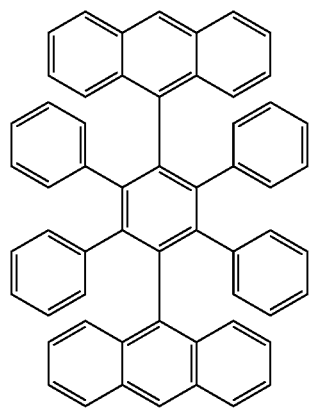
(1-30)
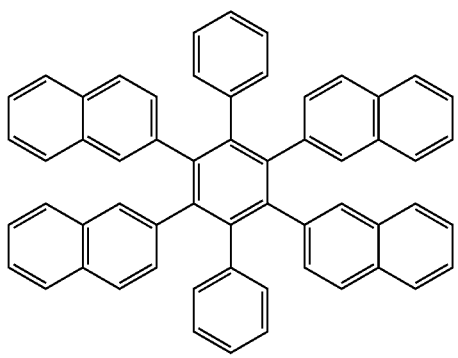
(1-31)
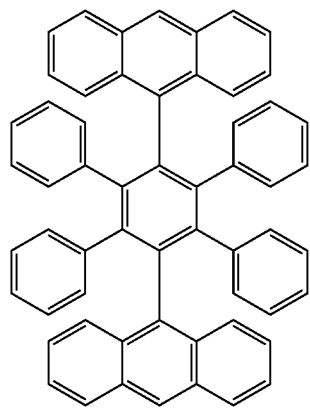
(1-32)
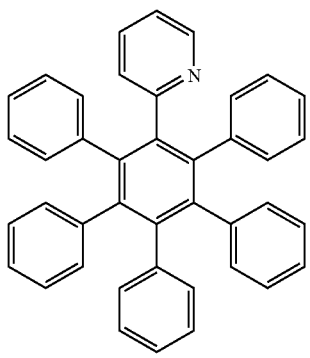

-continued
(1-33)
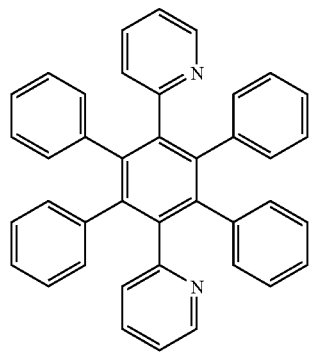
(1-34)
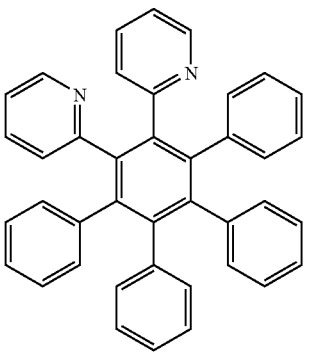
(1-35)
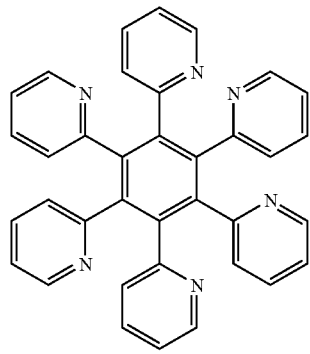
(1-36)
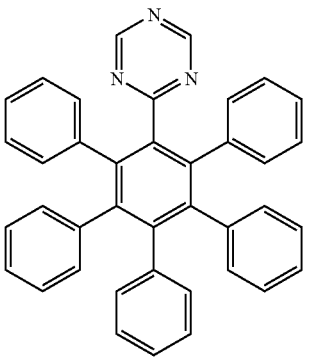
(1-37)
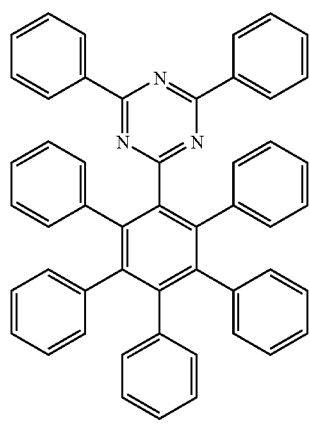
(1-38)
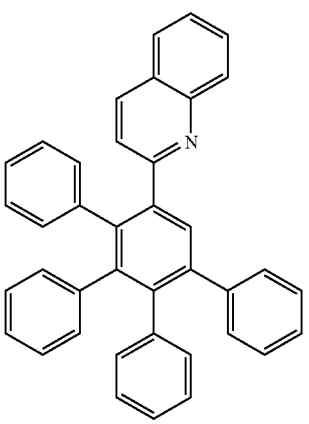
(1-39)
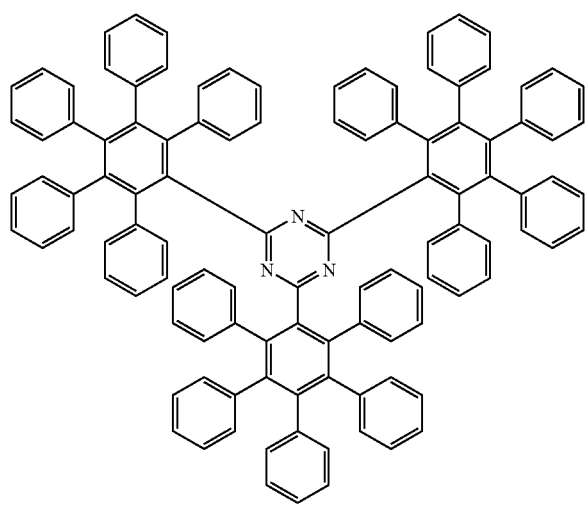
(1-40)
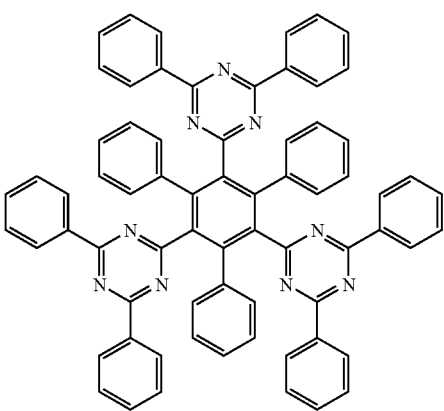

-continued
(1-41)
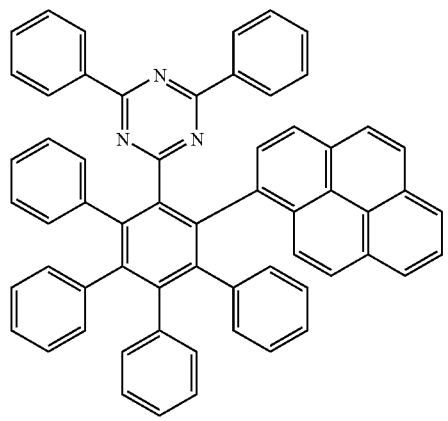
(1-42)
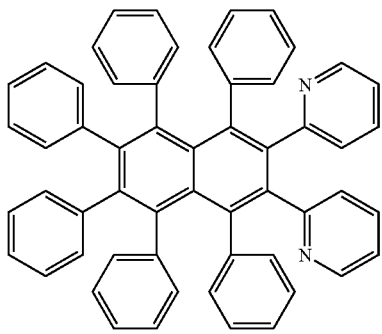
(1-43)
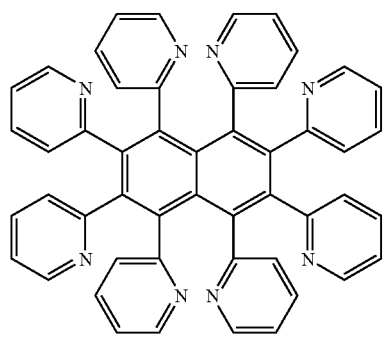
(1-44)
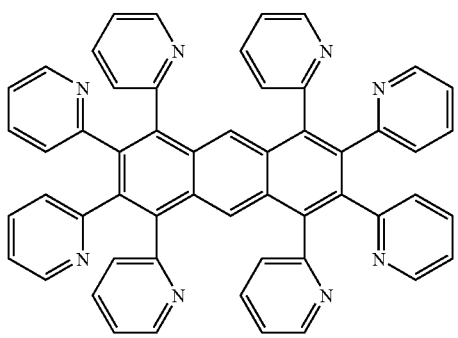
(1-45)
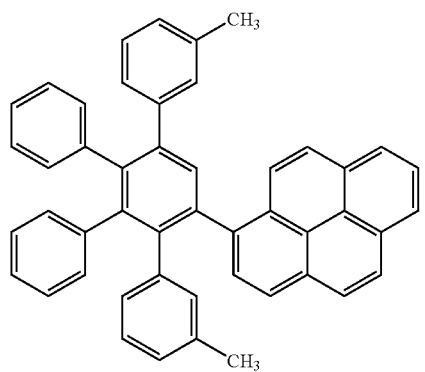
(1-46)
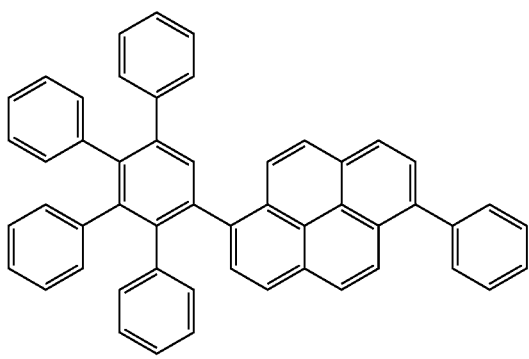
(1-47)
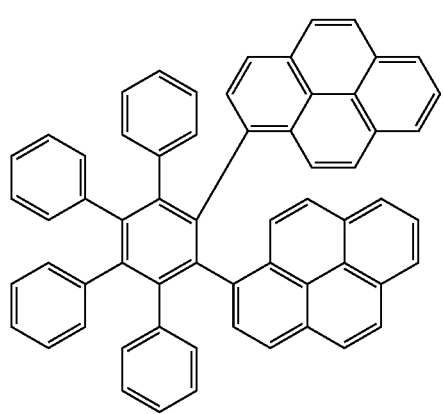
(1-48)
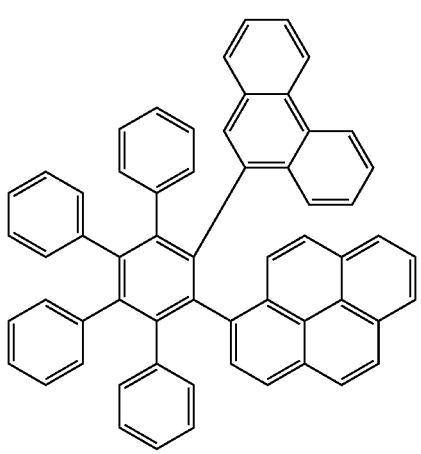

-continued
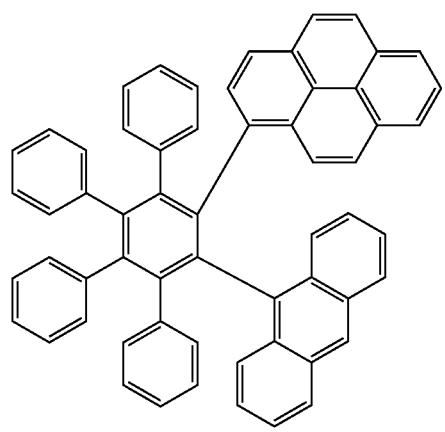
(1-49)
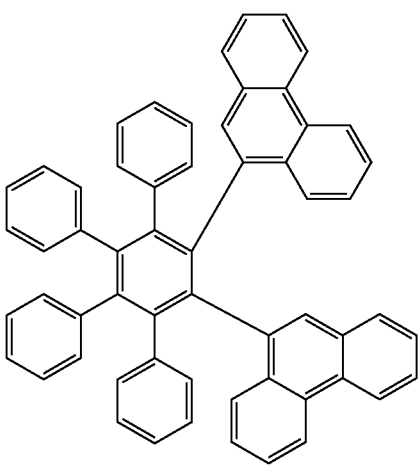
(1-50)
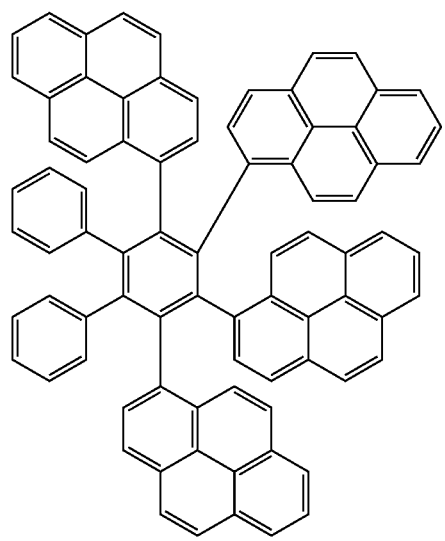
(1-51)
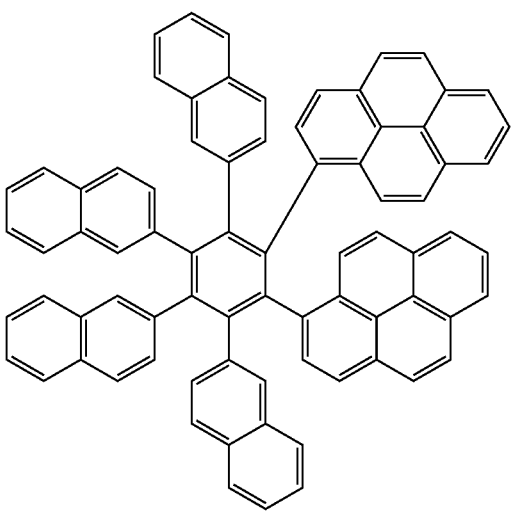
(1-52)
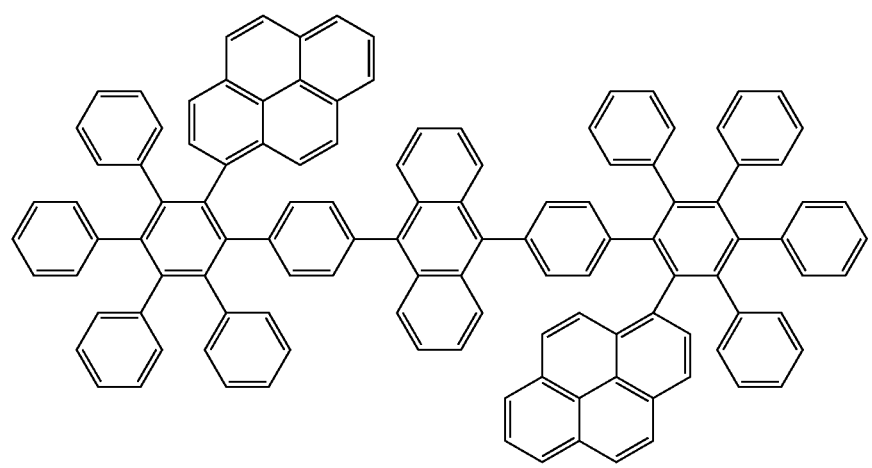
(1-53)

(1-54)
(1-55)
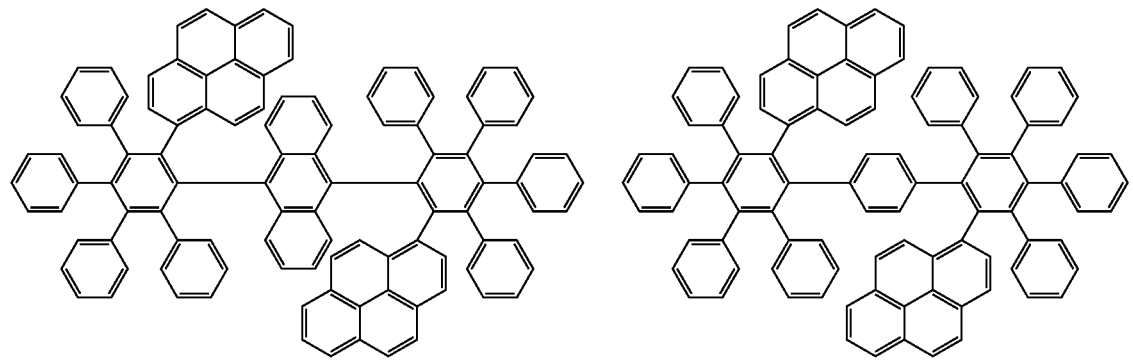
(1-56)
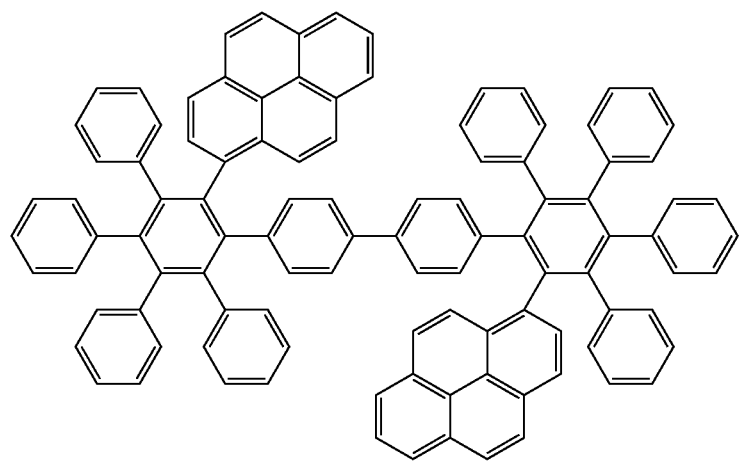
(1-57)
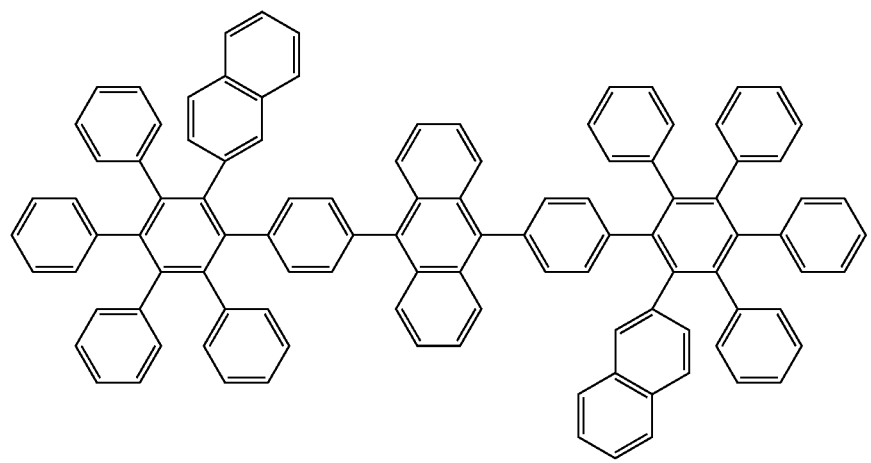

-continued
(1-58)
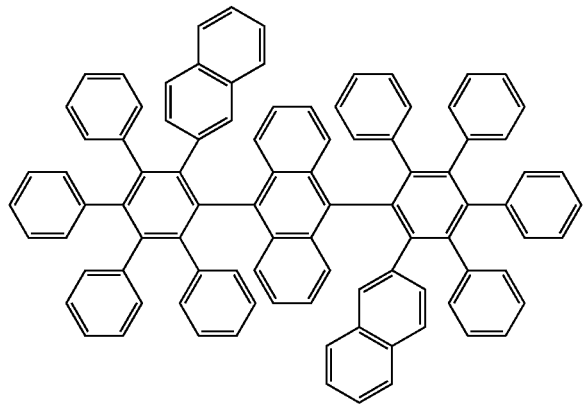
(1-59)
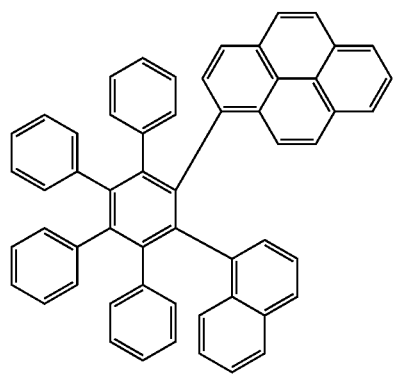
(1-60)
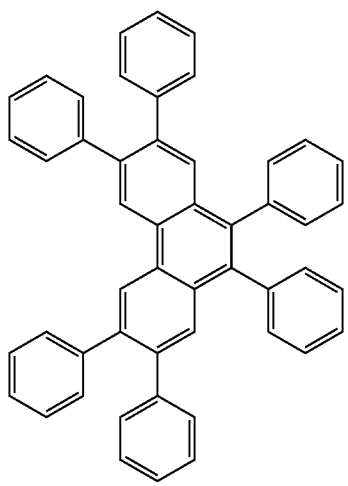
(1-61)
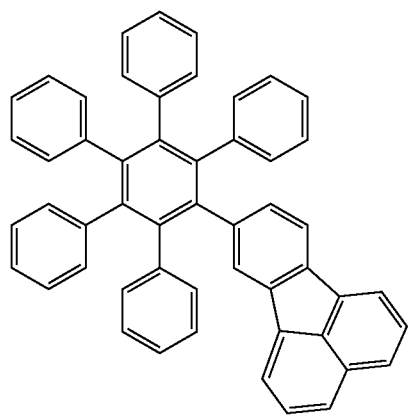
(1-62)
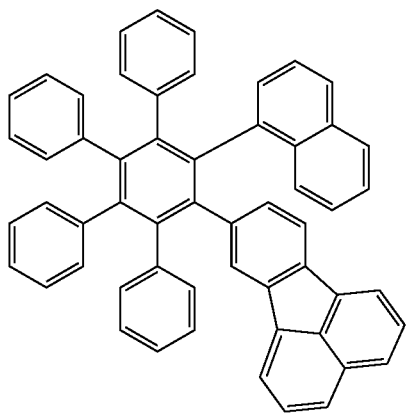
(1-63)
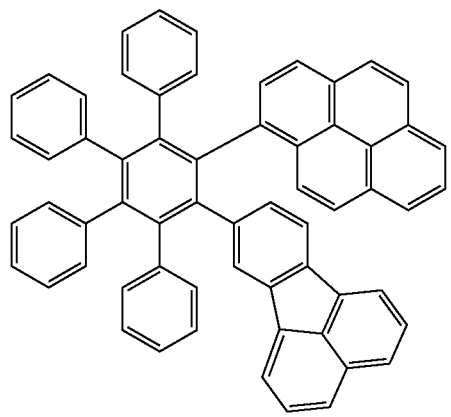

-continued
(1-64)
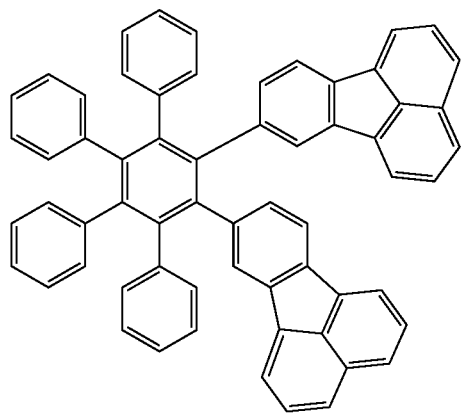
(1-65)
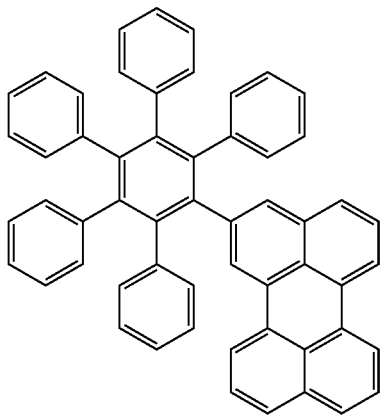
(1-66)
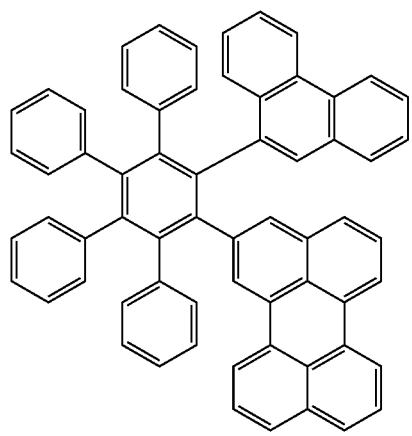
(1-67)
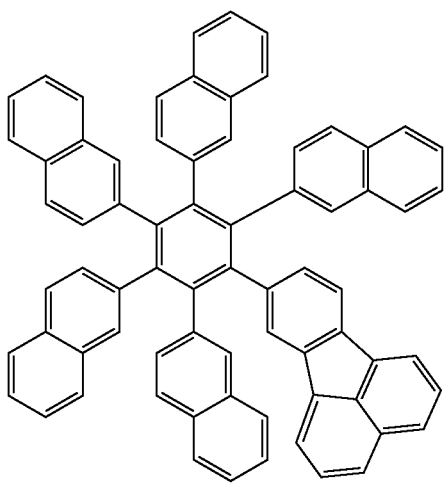
(1-68)
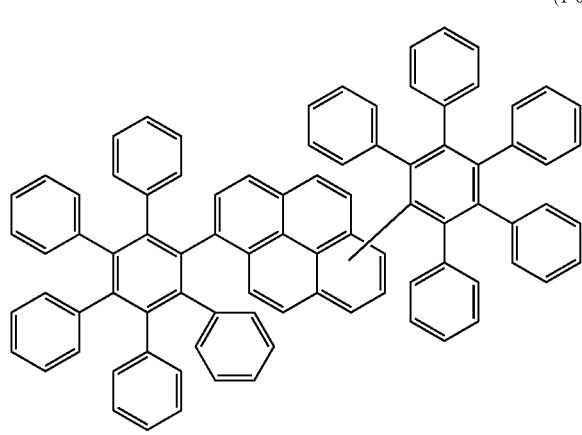
(1-69)
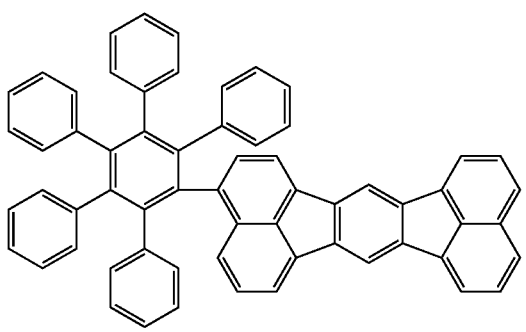

(1-70)
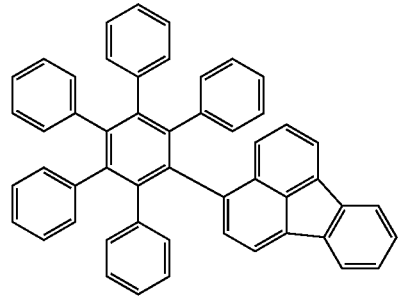
(1-71)
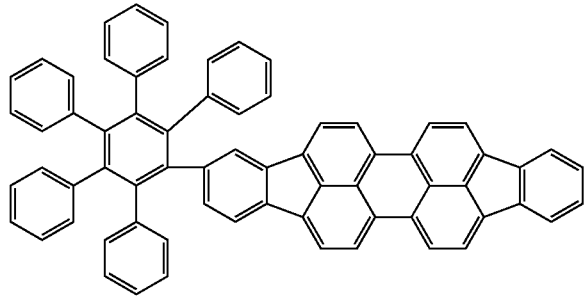
(1-72)
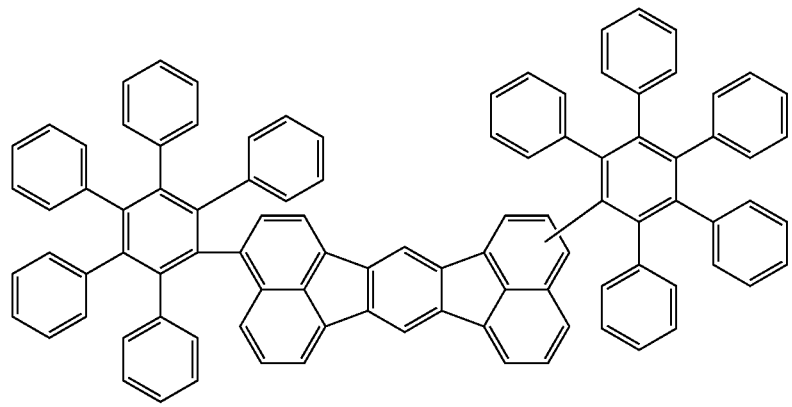
(1-73)
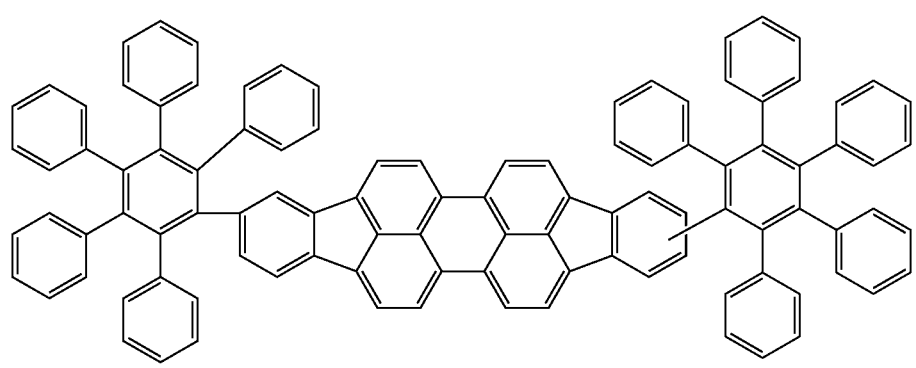

(1-74)
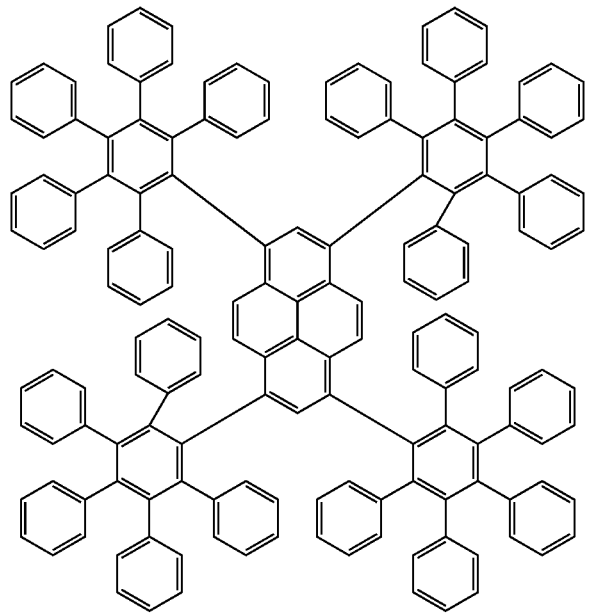
(1-75)
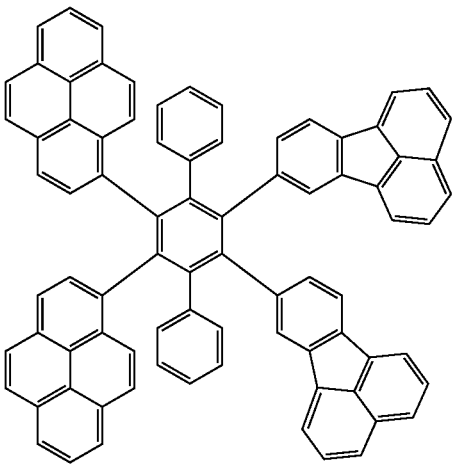
(1-76)
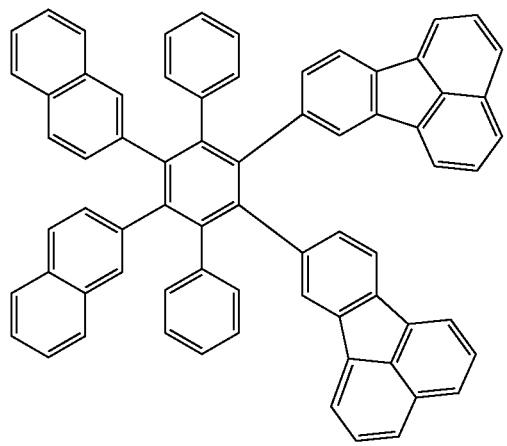
(1-77)
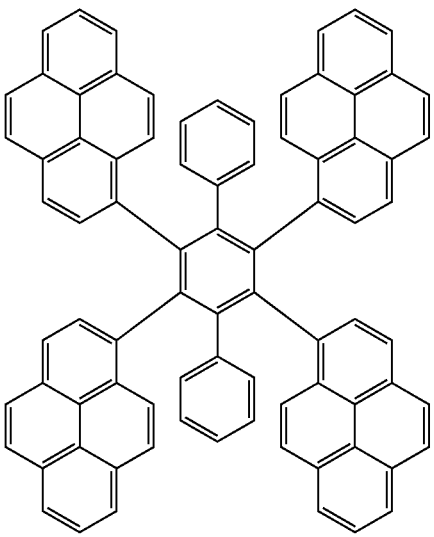

-continued
(1-78)
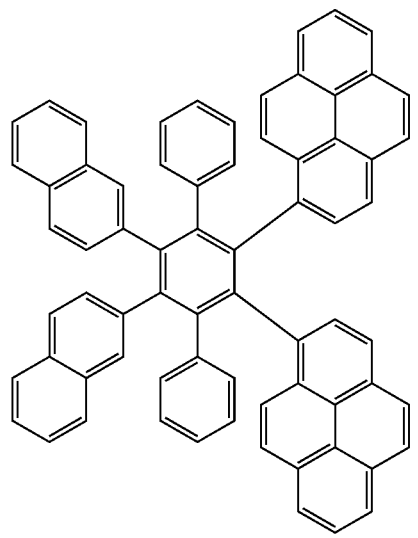
(1-79)
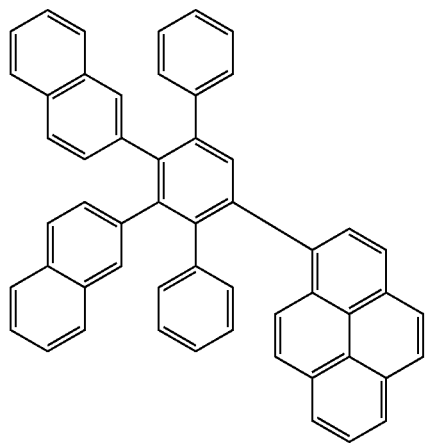
(1-80)
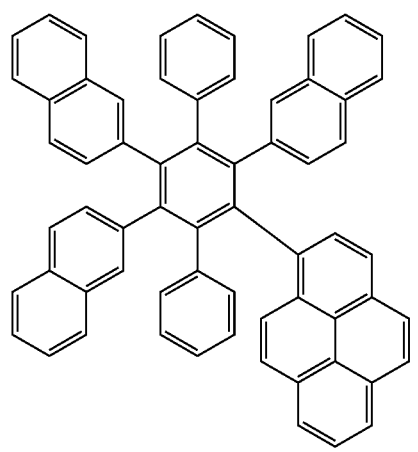
(1-81)
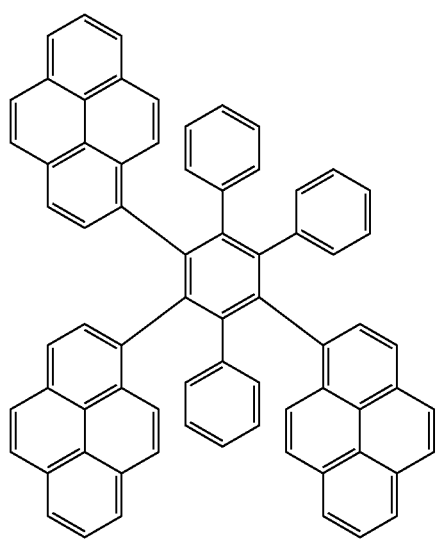
(1-82)
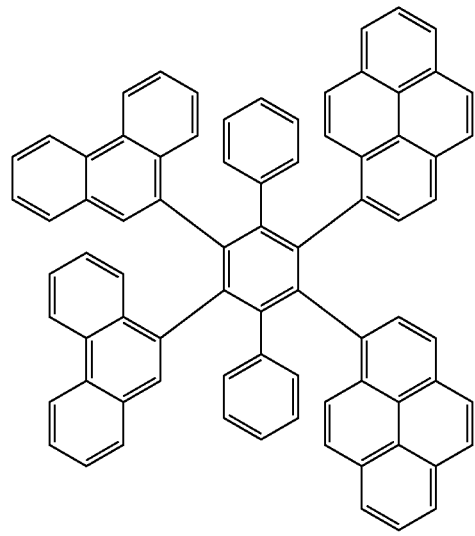
(1-83)
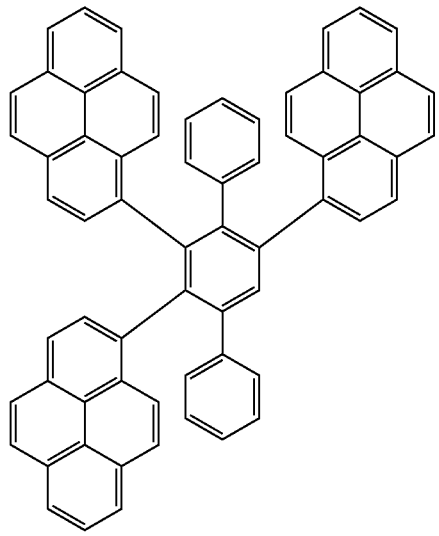

-continued
(1-84)
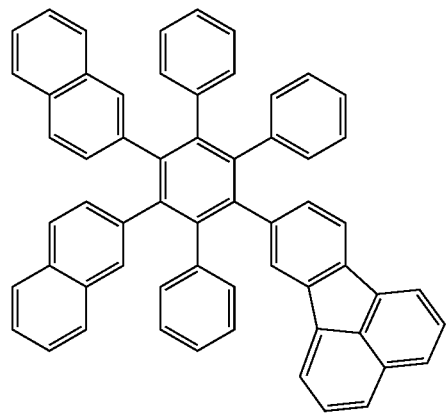
(1-85)
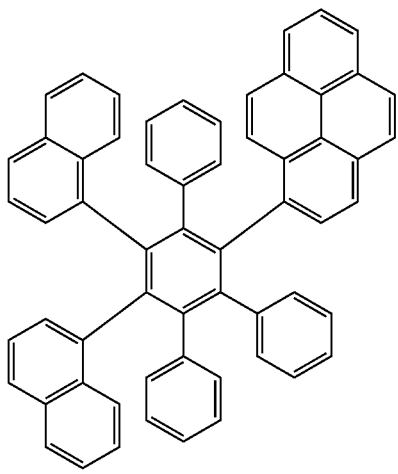
(1-86)
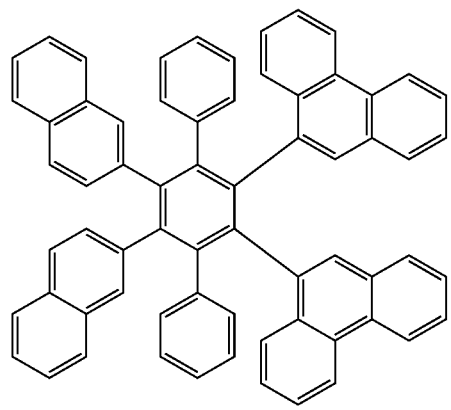
(1-87)
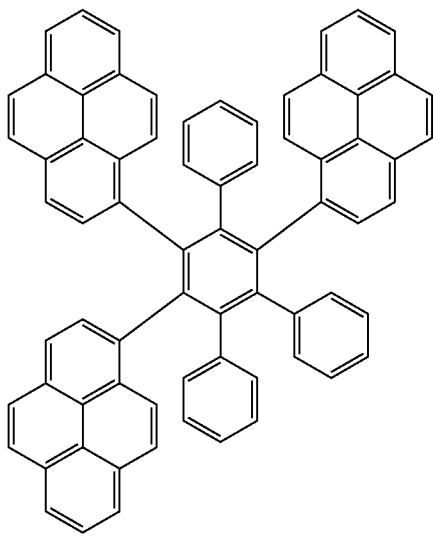
(1-88)
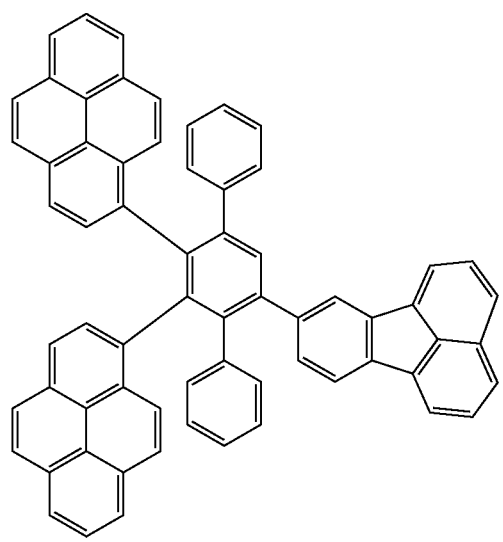
(1-89)
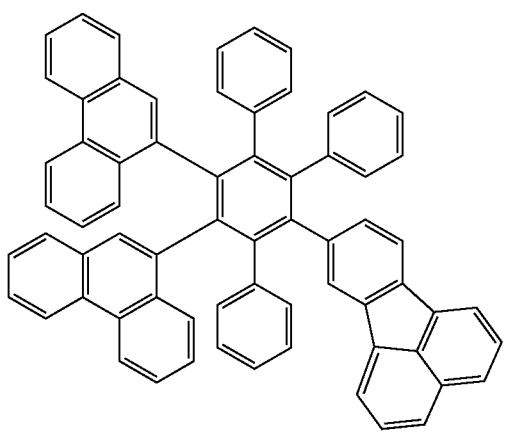

-continued
(1-90)
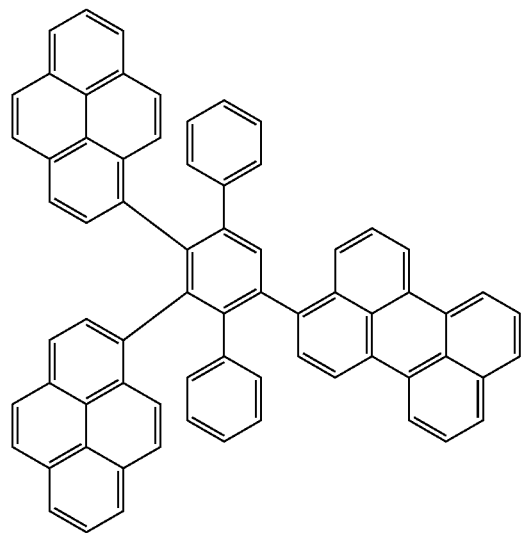
(1-91)
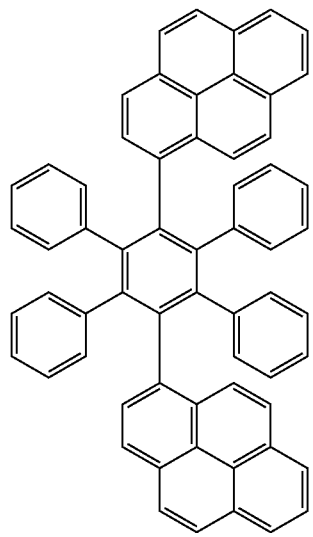
(1-92)
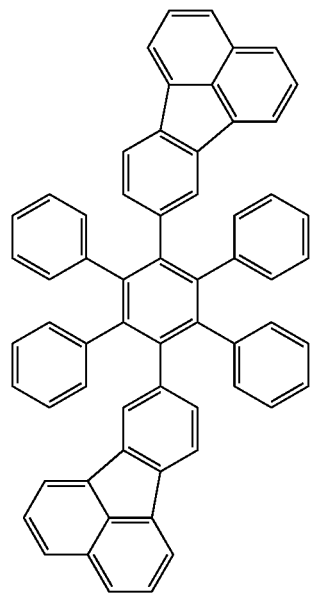
(1-93)
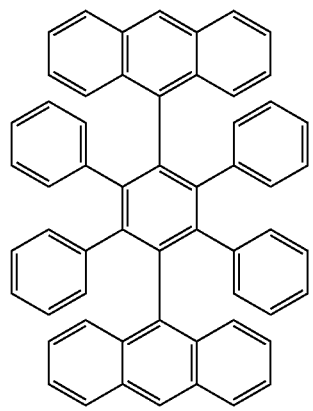
(1-94)
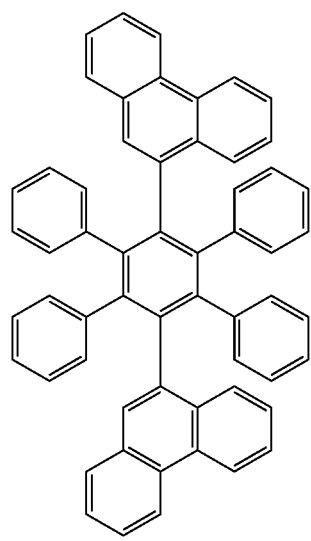
(1-95)
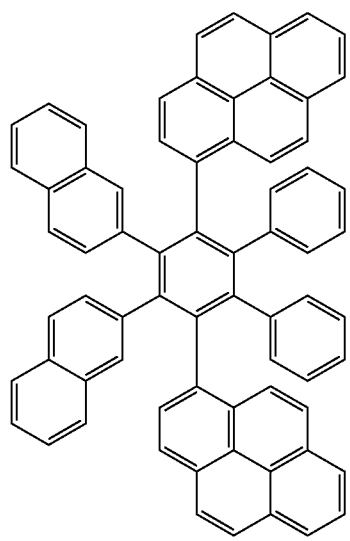

The compounds represented by the general formulae (1)-(6) may be purified. Purification methods are not particularly limited but may be a recrystallization method, a column chromatography method, a sublimation purification method, etc.

The sublimation purification methods are known, and may be a method described, for instance, in "Lecture One on Experimental Chemistry, Basic Operations [I]" issued by Maruzen Co., Ltd. pp. 425 to 430, methods described in JP 5-269371 A, JP 6-263438 A, JP 7-24205 A, JP 7-204402 A, JP 11-171801 A, JP 2000-93701 A, JP 200048955 A, JP 62-22960 B, JP 2583306 B, JP 2706936 B, etc. The sublimation purification may be carried out in vacuum or in a flow of an inert gas such as nitrogen, argon, etc. A vacuum pump for carrying out the sublimation purification in vacuum is not particularly restrictive, but may be a rotary pump, a turbo molecular pump, a diffusion pump, etc.

The compound (1) may be synthesized by known methods described in Tetrahedron, 1997, 53, No. 45, p. 15349; J. Am. Chem. Soc., 1996, 118, p. 741; J. Org. Chem. Soc., 1986, 51, p. 979; Angew. Chem. Int. Ed. Engl., 1997, 36, p. 631; Indian J. Chem. Sect. B, 2000, 39, p. 173; Org. Synth. Coll. Vol. 5, 1973, p. 604; Chem. Ber., 1960, 93, p. 1769, etc.

Although the light-emitting device of the present invention is not particularly limited with respect to a system and a driving method therefore, use thereof, etc., the light-emitting device preferably has a structure that uses the compound (1) as a light-emitting material, or as a host material, an electron-injecting material, an electron-transporting material, a hole-injecting material and/or a hole-transporting material. Typically known as the light-emitting devices are organic electroluminescence (EL) devices.

The light-emitting device of the present invention comprises a light-emitting layer and a plurality of organic layers comprising a light-emitting layer between a pair of electrodes (a positive electrode and a negative electrode). The light-emitting layer or at least one of the organic layers comprises the compound (1). When the compound of the present invention is used as a light-emitting material, the amount of the compound (1) in the layer comprising the compound (1) is preferably 0.1 to 100% by mass, more preferably 0.5 to 100% by mass. When the compound (1) is used as a host material, the amount of the compound (1) is preferably 10 to 99.9% by mass, more preferably 20 to 99.5% by mass.

The formation of a layer comprising the compound (1) is not particularly limited, and the layer may be formed by a resistance-heating vapor deposition method, an electron beam method, a sputtering method, a molecular-stacking method, a coating method, an inkjet-printing method, a printing method, a transferring method, an electrophotography method, etc. Preferable among them are a resistance-heating vapor deposition method, a coating method and a printing method from the viewpoints of properties and production cost of the light-emitting device.

The light-emitting device of the present invention may comprise functional layers such as a hole-injecting layer, a hole-transporting layer, an electron-injecting layer, an electron-transporting layer, a protective layer, etc., in addition to the light-emitting layer. The functional layers may have other functions. The compound (1) may be contained in any of these layers. Each component of the light-emitting device of the present invention is described in detail below.

(A) Positive Electrode

The positive electrode acts to supply holes to the hole-injecting layer, the hole-transporting layer, the light-emitting layer, etc. The positive electrode is generally made of a pure metal, an alloy, a metal oxide, an electrically conductive compound, a mixture thereof, etc., preferably made of a material having a work function of 4 eV or more. Examples of materials for the positive electrode include metals such as gold, silver, chromium nickel and these alloys; electrically conductive metal oxides such as tin oxide, zinc oxide, indium oxide and indium tin oxide (ITO); mixtures and laminations of the metals and the electrically conductive metal oxides; electrically conductive inorganic compounds such as copper iodide and copper sulfide; electrically conductive organic compounds such as polyaniline, polythiophene and polypyrrole; laminates of the electrically conductive organic compounds and ITO; etc. The positive electrode is preferably made of electrically conductive metal oxides, particularly ITO, from the viewpoints of productivity, electron conductivity, transparency, etc.

A method for forming the positive electrode may be selected depending on the material used therefore. For example, the positive electrode made of ITO may be formed by an electron beam method, a sputtering method, a resistance-heating vapor deposition method, a chemical reaction method such as a sol-gel method, a coating method using a dispersion containing indium tin oxide, etc. The positive electrode may be subjected to a washing treatment, etc., to lower the driving voltage, or to increase the light-emitting efficiency of the light-emitting device. For example, in the case of the positive electrode of ITO, a UV-ozone treatment and a plasma treatment are effective. The positive electrode preferably has sheet resistance of a few hundred Ω/square or less. Although the thickness of the positive electrode may be appropriately determined depending on the material used therefore, it is in general preferably 10 nm to 5 μm, more preferably 50 nm to 1 μm, most preferably 100 to 500 nm.

The positive electrode is generally disposed on a substrate made of soda lime glass, non-alkali glass, transparent resins, etc. The glass substrate is preferably made of non-alkali glass to reduce ion elution. In the case of using the soda lime glass, a barrier coating of silica, etc. is preferably formed thereon beforehand. The thickness of the substrate is not particularly limited as long as it has sufficient strength. In the case of the glass substrate, the thickness of the substrate is generally 0.2 mm or more, preferably 0.7 mm or more.

(B) Negative Electrode

The negative electrode acts to supply electrons to the electron-injecting layer, the electron-transporting layer, the light-emitting layer, etc. Materials for the negative electrode may be selected from pure metals, alloys, metal halides, metal oxides, electrically conductive compounds, mixtures thereof, etc., depending on ionization potential, stability, adhesion to a layer adjacent to the negative electrode such as the light-emitting layer, etc. Examples of materials for the negative electrode include alkali metals such as Li, Na and K, and fluorides and oxides thereof; alkaline earth metals such as Mg and Ca and fluorides and oxides thereof; gold; silver; lead; aluminum; alloys and mixtures of sodium and potassium; alloys and mixtures of lithium and aluminum; alloys and mixtures of magnesium and silver; rare earth metals such as indium and ytterbium; mixtures thereof; etc. The negative electrode is preferably made of a material having a work function of 4 eV or less, more preferably made of aluminum, an alloy or a mixture of lithium and aluminum, or an alloy and a mixture of magnesium and silver.

The negative electrode may have a single-layer structure or a multi-layer structure. A preferred multi-layer structure is aluminum/lithium fluoride, aluminum/lithium oxide, etc. The negative electrode may be formed by an electron beam method, a sputtering method, a resistance-heating vapor deposition method, a coating method, etc. A plurality of materials may be simultaneously deposited by the vapor deposition method. The negative electrode of an alloy may be formed by simultaneously depositing a plurality of metals, or by depositing their alloy. The negative electrode preferably has a sheet resistance of a few hundred Ω/square or less. Although the thickness of the negative electrode may be appropriately determined depending on the material used therefore, it is in general preferably 10 nm to 5 μm, more preferably 50 nm to 1 μm, most preferably 100 nm to 1 μm.

(C) Hole-injecting Layer and Hole-transporting Layer

Materials used for the hole-injecting layer and the hole-transporting layer are not particularly limited as long as they have any functions of injecting holes provided from the positive electrode into the light-emitting layer; transporting holes to the light-emitting layer; and blocking electrons provided from the negative electrode. Their examples include carbazole, triazole, oxazole, oxadiazole, imidazole, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, aromatic dimethylidyne compounds, porphyrin compounds, polysilane compounds, poly(N-vinylcarbazole), aniline copolymers, electrically conductive polymers and oligomers such as oligothiophenes and polythiophenes, organic silane compounds, the compound (1), derivatives thereof, carbon, etc.

Each of the hole-injecting layer and the hole-transporting layer may be a single layer made of one or more materials, or a multi-layer made of the same or different materials. The hole-injecting layer and the hole-transporting layer may be formed by a vacuum deposition method, an LB method, a coating method using a solution or a dispersion containing the above material such as a spin-coating method, a casting method and a dip-coating method, an inkjet-printing method, a printing method, a transferring method, an electrophotography method, etc. A solution and a dispersion used in the coating method may contain a resin. Examples of such resins include poly(vinyl chloride), polycarbonates, polystyrene, poly(methyl methacrylate), poly(butyl methacrylate), polyesters, polysulfones, poly(phenylene oxide), polybutadiene, poly(N-vinylcarbazole), hydrocarbon resins, ketone resins, phenoxy resins, polyamides, ethyl cellulose, poly(vinyl acetate), ABS resins, polyurethanes, melamine resins, unsaturated polyester resins, alkyd resins, epoxy resins, silicone resins, etc. Although the thickness of each of the hole-injecting layer and the hole-transporting layer is not particularly limited, it is in general preferably 1 nm to 5 μm, more preferably 5 nm to 1 μm, particularly 10 to 500 nm.

(D) Light-emitting Layer

In the light-emitting layer, holes injected from the positive electrode, the hole-injecting layer or the hole-transporting layer and electrons injected from the negative electrode, the electron-injecting layer or the electron-transporting layer are recombined to emit light when an electric field is applied to the light-emitting device. Light-emitting materials and fluorescent compounds for the light-emitting layer are not particularly limited as long as they have functions of receiving holes provided from the positive electrode, etc.; receiving electrons provided from the negative electrode, etc.; transporting charges; and recombining holes and electrons to emit light when an electric field is applied to the light-emitting device. Examples of the light-emitting materials include benzoxazole; benzoimidazole; benzothiazole; styrylbenzene; polyphenyl; diphenylbutadiene; tetraphenylbutadiene; naphthalimido; coumarin; perynone; oxadiazole; aldazine; pyralidine; cyclopentadiene; bis(styryl)anthracene; quinacridon; pyrrolopyridine; thiadiazolopyridine; cyclopentadiene; styrylamine; aromatic dimethylidine compounds; pyrromethene; condensed aromatic compounds such as anthracene, pyrene, fluoranthene, perylene; metal complexes such as 8-quinolinol derivative metal complexes; high-molecular-weight, light-emitting materials such as polythiophene, polyphenylene and polyphenylenevinylene; organic silane compounds; the compound (1); derivatives thereof; etc.

The light-emitting layer may be made of one or more materials. The light-emitting device of the present invention may comprise one or more light-emitting layers. In a case where the light-emitting device comprises a plurality of light-emitting layers, each of the light-emitting layers may be made of one or more materials, and may emit light with a different color to provide white light. The single light-emitting layer may provide white light.

The light-emitting layer may be formed by a resistance-heating vapor deposition method; an electron beam method; a sputtering method; a molecular-stacking method; a coating method such as a spin-coating method, a casting method and a dip-coating method; an inkjet-printing method; a printing method; an LB method; a transferring method; an electrophotography method; etc. Preferable among them are the resistance-heating vapor deposition method and the coating method. Although the thickness of the light-emitting layer is not particularly limited, it is in general preferably 1 nm to 5 μm, more preferably 5 nm to 1 μm, particularly 10 to 500 nm.

(E) Electron-injecting Layer and Electron-transporting Layer

Materials used for the electron-injecting layer and the electron-transporting layer are not particularly limited as long as they have any functions of injecting electrons provided from the negative electrode into the light-emitting layer; transporting electrons to the light-emitting layer; and blocking holes provided from the positive electrode. Examples of such materials include triazole; oxazole; oxadiazole; imidazole; fluorenone; anthraquinodimethane; anthrone; diphenylquinone; thiopyran dioxide; carbodiimide; fluorenylidenemethane; distyrylpyrazine; tetracarboxylic anhydrides having such aromatic rings as a naphthalene ring and a perylene ring; phthalocyanine; metal complexes such as 8-quinolinol derivative metal complexes, metallophthalocyanines and metal complexes containing benzoxazole or benzothiazole as a ligand; metals such as aluminum, zinc, gallium, beryllium, magnesium; organic silane compounds; the compound (1); derivatives thereof; etc.

Each of the electron-injecting layer and the electron-transporting layer may have a structure of single-layer made of one or more materials, or multi-layers made of the same or different materials. The electron-injecting layer and the electron-transporting layer may be formed by a vacuum deposition method; an LB method; a coating method using a solution or a dispersion containing the above material, such as a spin-coating method, a casting method and a dip-coating method; an inkjet-printing method; a printing method; a transferring method; an electrophotography method; etc. The solution and the dispersion used in the coating method may contain a resin. Examples of such resins may be the same as those for the hole-injecting layer and the hole-transporting layer. Although the thickness of each of the electron-injecting layer and the electron-transporting layer is not particularly limited, it is in general preferably 1 nm to 5 μm, more preferably 5 nm to 1 μm, particularly 10 to 500 nm.

(F) Protective Layer

The protective layer acts to shield the light-emitting device from the penetration of moisture, oxygen, etc. that deteriorates the device. Examples of materials for the protective layer include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; metal fluorides such as $MgF_2$, LiF, $AlF_3$ and $CaF_2$; nitrides such as $SiN_x$ and $SiO_xN_y$; polyethylene; polypropylene; polymethyl methacrylate; polyimides; polyureas; polytetrafluoroethylene; polychlorotrifluoroethylene; polydichlorodifluoroethylene; copolymers of chlorotrifluoroethylene and dichlorodifluoroethylene; copolymers of tetrafluoroethylene and at least one comonomer; fluorine-containing copolymers having main chains with cyclic structures; moisture-absorbing materials having a water absorption of 1% or more; moisture-resistant materials having a water absorption of 0.1% or less; etc.

A method for forming the protective layer is not particularly limited. The protective layer may be formed by a vacuum deposition method, a sputtering method, a reactive sputtering method, a molecular beam epitaxy (MBE) method, a cluster ion beam method, an ion-plating method, a high-frequency excitation ion-plating method, a plasma polymerization method, a plasma CVD method, a laser CVD method, a thermal CVD method, a gas source CVD method, a coating method, a printing method, a transferring method, etc.

The present invention will be specifically described below with reference to Examples without intention of restricting the scope of the present invention.

SYNTHESIS EXAMPLE 1

Synthesis of Compound (1-1)

10 ml of o-xylene was added to 0.5 g of 1-ethynylpyrene and 0.85 g of tetraphenylcyclopentadienone and stirred under reflux for 3 hours. The resultant reaction product solution was cooled to room temperature, and 50 ml of methanol was added thereto to precipitate a solid. The solid was separated by filtration, and purified by a silica gel column chromatography (hexane/chloroform=5/1), to obtain 1.1 g of a white solid. Mass spectrum measurement confirmed that the white solid was Compound (1-1). This result suggested that Compound (1-1) was obtained by the following reaction.

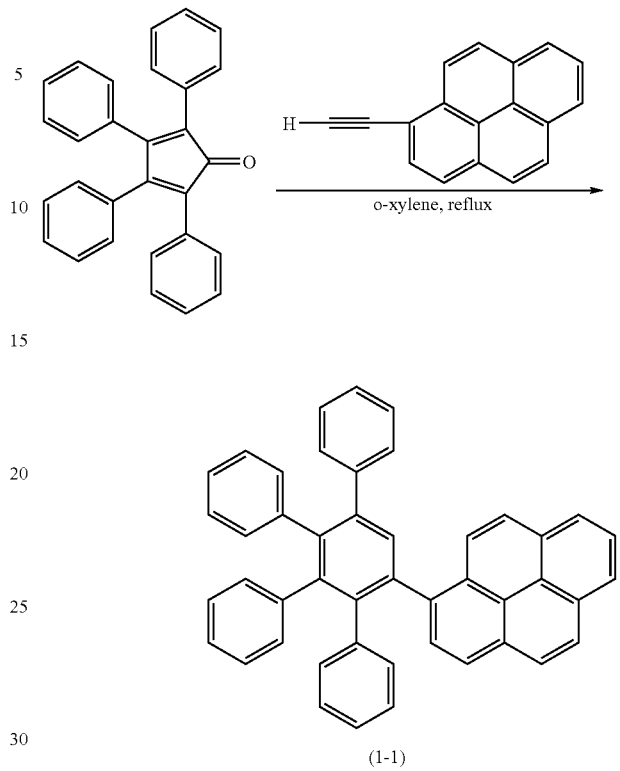

SYNTHESIS EXAMPLE 2

Synthesis of Compound (1-47)

50 ml of diphenyl ether was added to 1 g of the following Compound A and 1.35 g of tetraphenylcyclopentadienone and stirred under reflux for 30 hours. The resultant reaction product solution was cooled to room temperature, and 100 ml of methanol was added thereto to precipitate a solid. The solid was separated by filtration, and purified by a silica gel column chromatography (chloroform), to obtain 1.3 g of a white solid. Mass spectrum measurement confirmed that the white solid was Compound (1-47). This result suggested that Compound (1-47) was obtained by the following reaction.

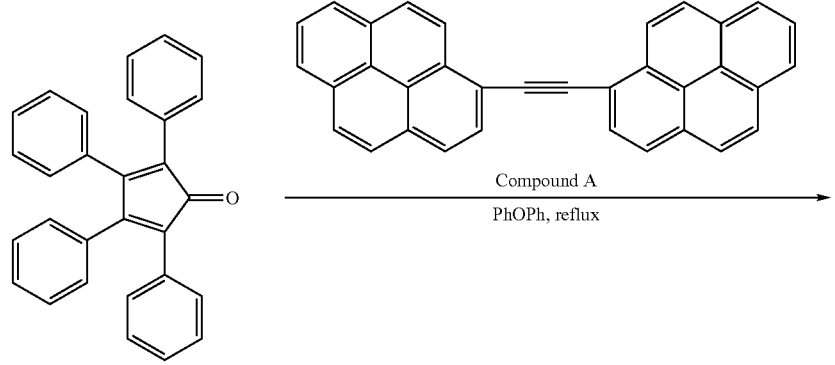

-continued

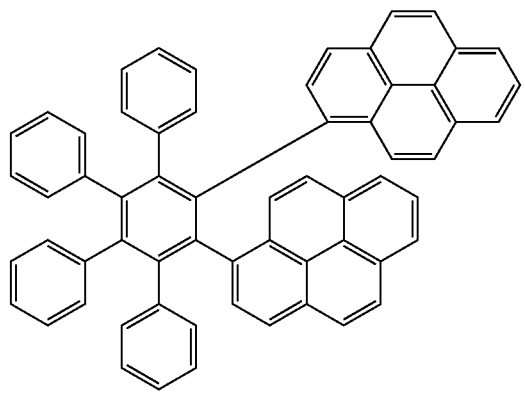

(1-47)

SYNTHESIS EXAMPLE 3

Synthesis of Compound (1-15)

50 ml of diphenyl ether was added to 1 g of the following Compound B and 3 g of tetraphenylcyclopentadienone and stirred under reflux for 10 hours. The resultant reaction product solution was cooled to room temperature, and 100 ml of methanol was added thereto to precipitate a solid. The solid was separated by filtration, and purified by a silica gel column chromatography (chloroform), to obtain 2.0 g of a white solid. Mass spectrum measurement confirmed that the white solid was Compound (1-15). This result suggested that Compound (1-15) was obtained by the following reaction.

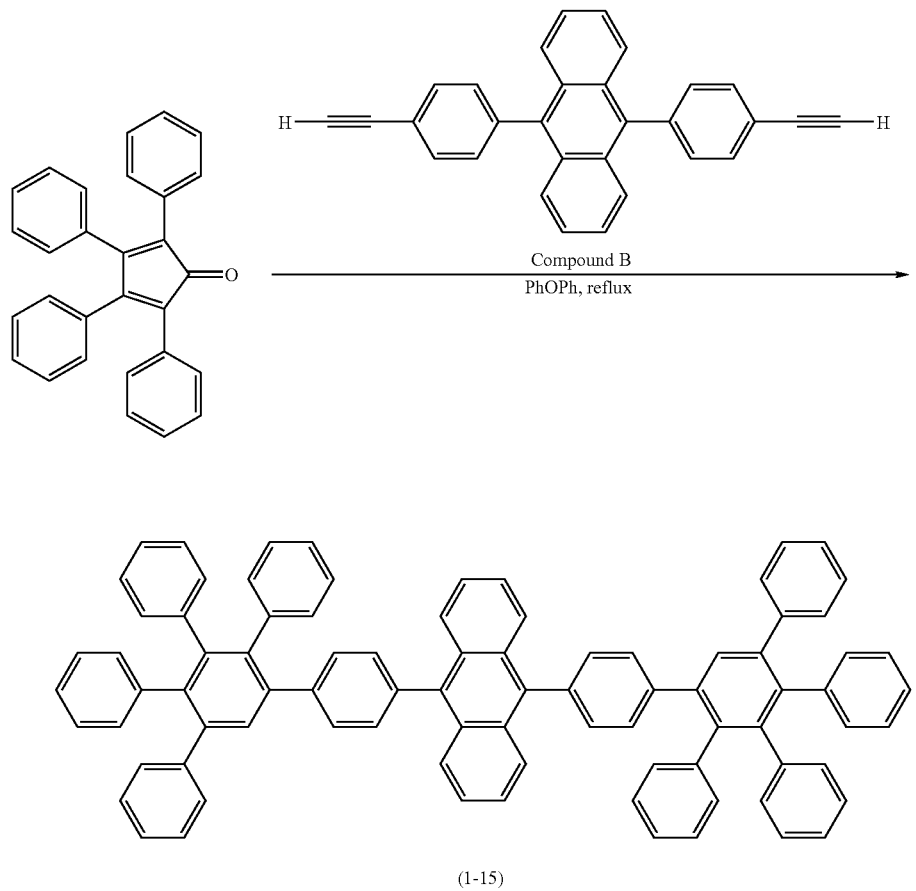

(1-15)

SYNTHESIS EXAMPLE 4

Synthesis of Compound (1-2)

10 ml of diphenyl ether was added to 0.5 g of the following Compound C and 0.85 g of tetraphenylcyclopentadienone and the resultant reaction mixture was stirred under reflux for 3 hours. The resultant reaction product solution was cooled to room temperature, and 50 ml of methanol was added thereto to precipitate a solid. The solid was separated by filtration, and purified by a silica gel column chromatography (hexane/chloroform=5/1), to obtain 1.0 g of a white solid. Mass spectrum measurement confirmed that the white solid was Compound (1-2). This result suggested that Compound (1-2) was obtained by the following reaction.

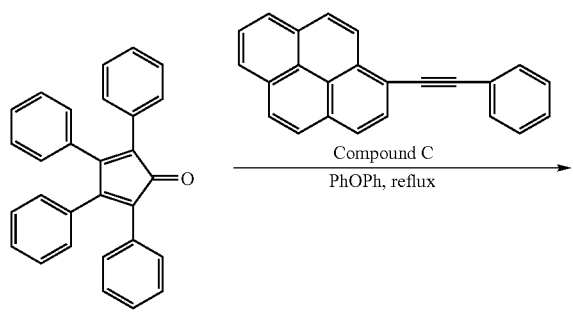

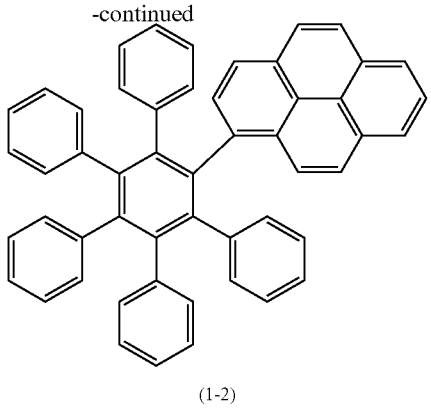

(1-2)

SYNTHESIS EXAMPLE 5

Synthesis of Compound (1-14)

50 ml of diphenyl ether was added to 0.5 g of the following Compound D and 3 g of tetraphenylcyclopentadienone and stirred under reflux for 10 hours. The resultant reaction product solution was cooled to room temperature, and 100 ml of methanol was added thereto to precipitate a solid. The solid was separated by filtration, and purified by a silica gel column chromatography (chloroform), to obtain 0.9 g of pale yellow solid. Mass spectrum measurement confirmed that the pale yellow solid was Compound (1-14). This result suggested that Compound (1-14) was obtained by the following reaction.

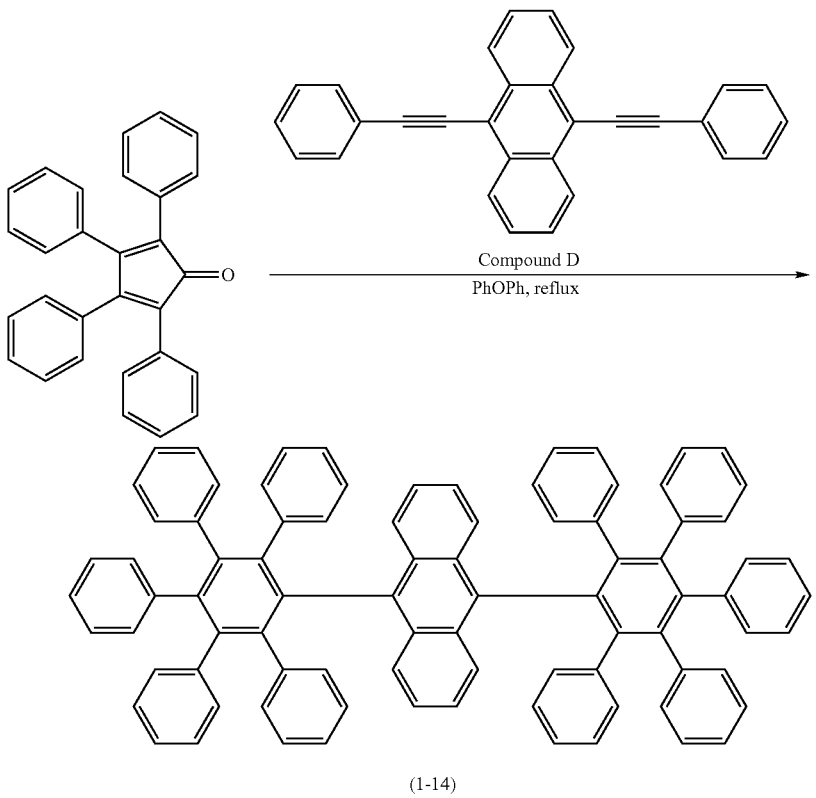

(1-14)

Compounds b-v used in the following Examples and Comparative Examples will be illustrated below.
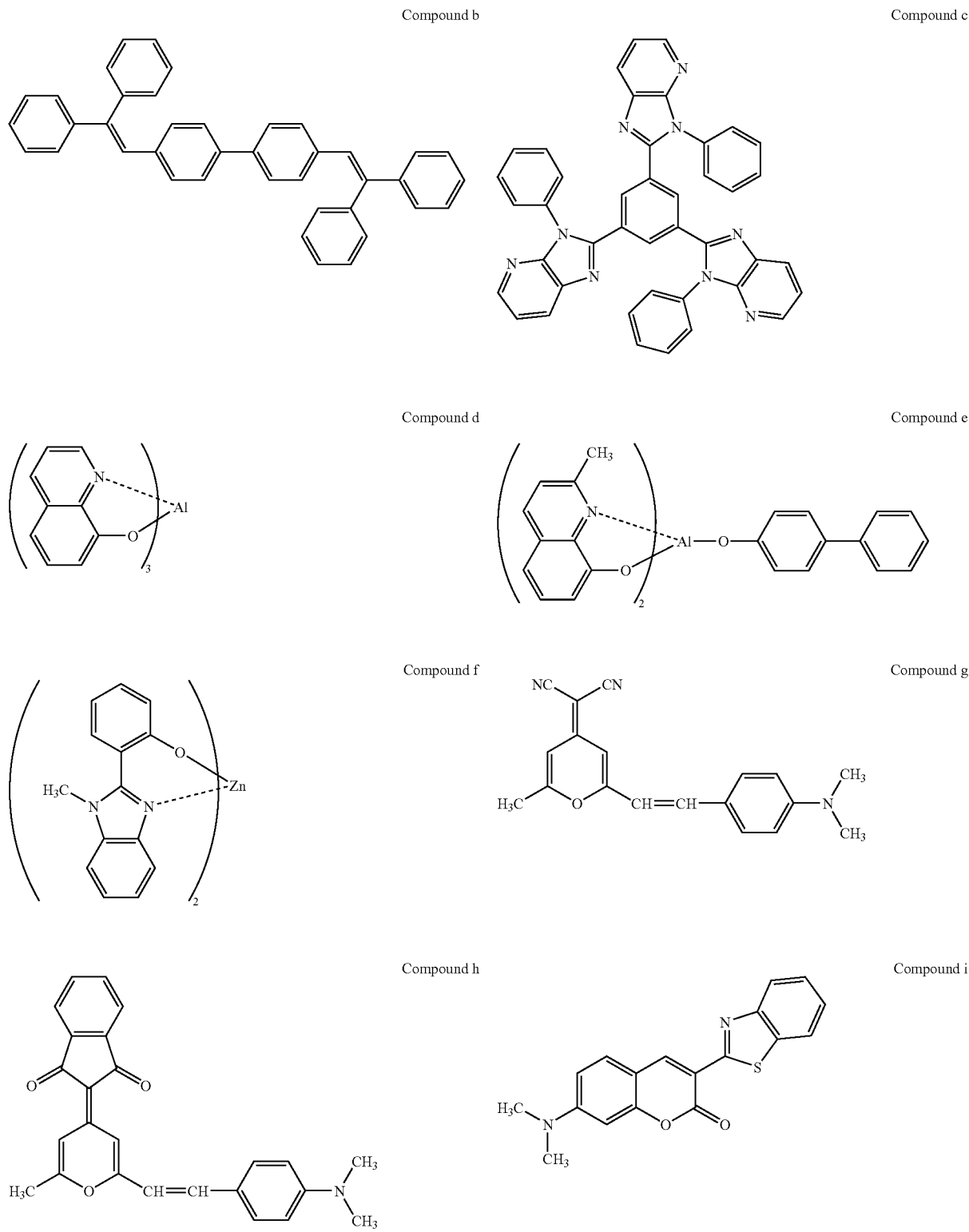

-continued
Compound j
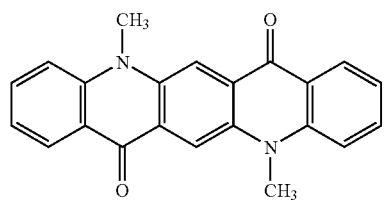
Compound k
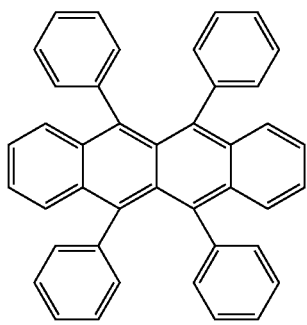
Compound m
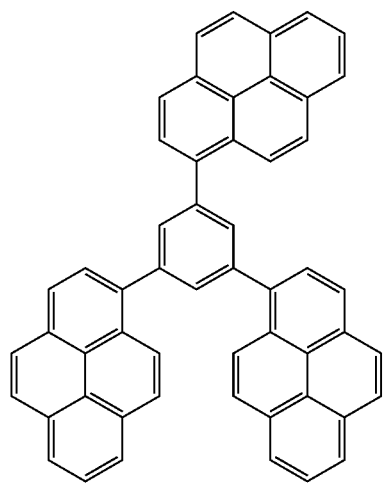
Compound n
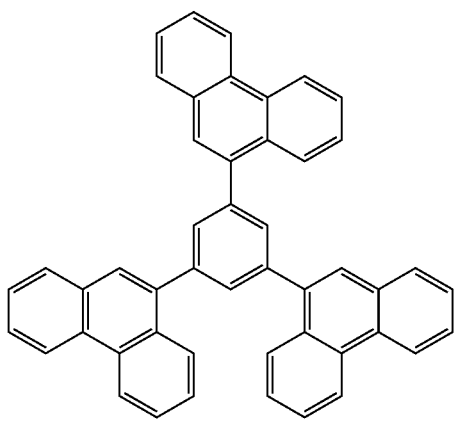
Compound o
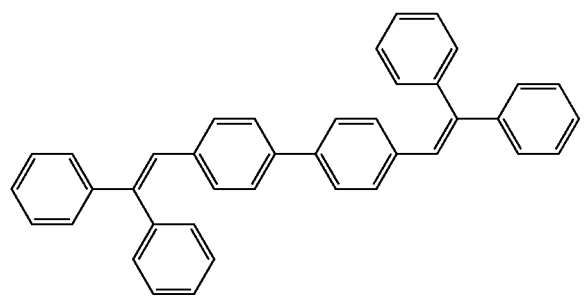
Compound p
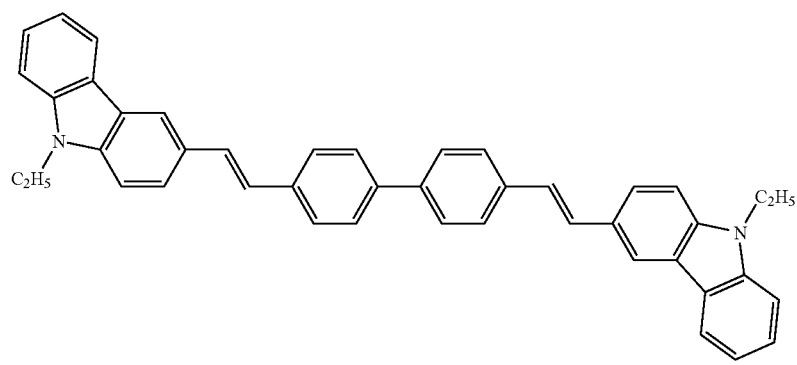

-continued
Compound q
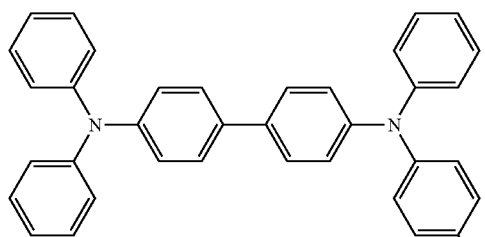
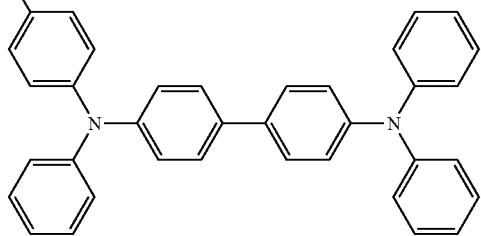
Compound r
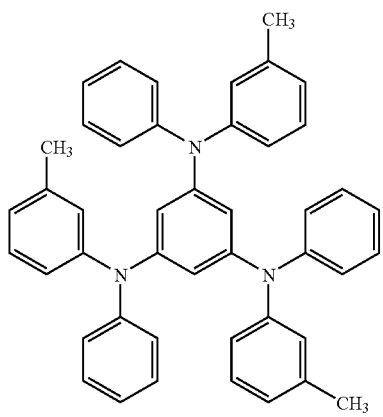
Compound s
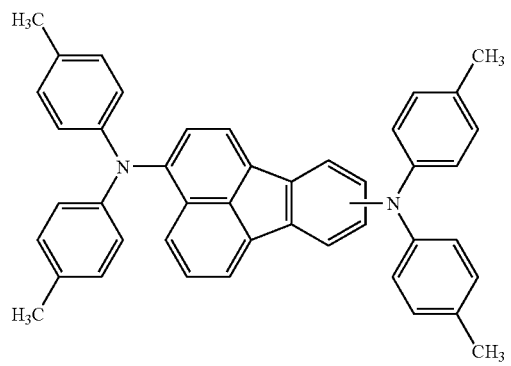
Compound t
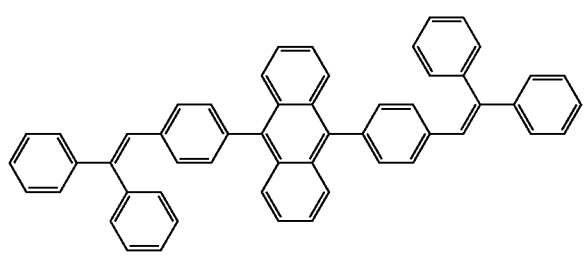
Compound u
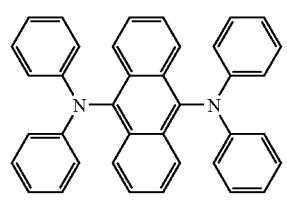
Compound v
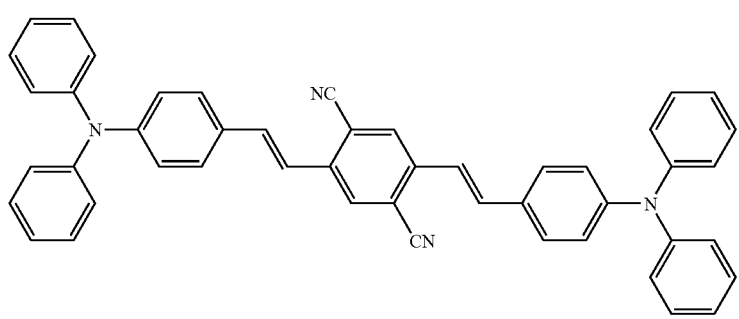

Comparative Example 1

N,N'-diphenyl-N,N'-di(α-naphthyl)benzidine (α-NPD) was vapor-deposited in a thickness of 40 nm on a cleaned ITO substrate placed in a deposition apparatus. The above distyryl compound (Compound b) was vapor-deposited in a thickness of 20 nm thereon, and the above azole compound (Compound c) was then vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device.

DC voltage was applied to the light-emitting device of Comparative Example 1 by "Source-Measure Unit 2400" available from Toyo Corporation to make it emit light, and the emitted light was measured with respect to luminance by "Luminance Meter BM-8" available from Topcon Corporation, and emission wavelength by "Spectral Analyzer PMA-11" available from Hamamatsu Photonics K. K. As a result, it was found that the light-emitting device of Comparative Example 1 emitted bluish green light with a chromaticity of (0.15, 0.20) at the maximum luminance of 1,130 cd/m². After leaving this light-emitting device in a nitrogen atmosphere for one day, the layer surface of the light-emitting device looked clouded.

Example 1

N,N'-diphenyl-N,N'-di(α-naphthyl)benzidine (α-NPD) was vapor-deposited in a thickness of 40 nm on a cleaned ITO substrate placed in a deposition apparatus. Compound (1-1) was vapor-deposited in a thickness of 20 nm thereon, and the azole compound (Compound c) was then vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.15, 0.10) at the maximum luminance of 4,370 cd/m². The external quantum efficiency of this light-emitting device was $\phi_{EL}=1.4\%$ in a calculated value. After leaving this light-emitting device in a nitrogen atmosphere for one day, the layer surface of the light-emitting device looked transparent.

Example 2

N,N'-diphenyl-N,N'-di(α-naphthyl)benzidine (α-NPD) was vapor-deposited in a thickness of 40 nm on a cleaned ITO substrate placed in a deposition apparatus. Compound (1-17) was vapor-deposited in a thickness of 20 nm thereon, and the azole compound (Compound c) was vapor-deposited in a thickness of 40 nm thereon. With a mask patterned for a desired light-emitting area of 4 mm×5 mm disposed on the resultant organic thin film magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.15, 0.14) at the maximum luminance of 2,920 cd/m². The external quantum efficiency of this light-emitting device was $\phi_{EL}=1.3\%$ in a calculated value. After leaving this light-emitting device in a nitrogen atmosphere for one day, the layer surface of the light-emitting device looked transparent.

Example 3

N,N'-diphenyl-N,N'-di(α-naphthyl)benzidine (α-NPD) was vapor-deposited in a thickness of 40 nm on a cleaned ITO substrate placed in a deposition apparatus. Compound (1-24) was vapor-deposited in a thickness of 20 nm thereon, and the azole compound (Compound c) was vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.15, 0.18) at the maximum luminance of 2,000 cd/m². The external quantum efficiency of this light-emitting device was $\phi_{EL}=1.3\%$ in a calculated value. After leaving this light-emitting device in a nitrogen atmosphere for one day, the layer surface of the light-emitting device looked transparent.

Example 4

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and 7,4-(dicyanomethylene)-2-methyl-6-(4-dimethylaminostyryl)-4H-pyran (DCM) were co-deposited in a thickness of 20 nm at a mass ratio of Compound (1-1)/DCM of 1000:5 thereon, and the azole compound (Compound c) was vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted white light with a chromaticity of (0.30, 0.32) at the maximum luminance of 4,300 cd/m². The external quantum efficiency of this light-emitting device was $\phi_{EL}=2.2\%$ in a calculated value. After leaving this light-emitting device in a nitrogen atmosphere for one day, the layer surface of the light-emitting device looked transparent.

Example 5

N,N'-diphenyl-N,N'-di(α-naphthyl)benzidine (α-NPD) was vapor-deposited in a thickness of 40 nm on a cleaned ITO substrate placed in a deposition apparatus. Tris(8-hydroxyquinolinato) aluminum (Alq) and DCM were co-deposited in a thickness of 5 nm at a mass ratio of Alq/DCM of 100:1 thereon, and Compound (1-1) was further vapor-deposited in a thickness of 15 nm thereon. The azole compound (Compound c) was then vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 5 nm on the organic thin film in the deposition apparatus, silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted white light with a chromaticity of (0.31, 0.33) at the maximum luminance of 4,400 cd/m². The external quantum efficiency of this light-emitting device was $\phi_{EL}$=2.3% in a calculated value. After leaving this light-emitting device in a nitrogen atmosphere for one day, the layer surface of the light-emitting device looked transparent.

Example 6

40 mg of poly(N-vinylcarbazole), 12 mg of 2-(4-t-butylphenyl)-5-(4-biphenyl)-1,3,4-oxadiazole and 1 mg of Compound (1-1) were dissolved in 2.5 ml of dichloroethane. The resultant solution was spin-coated to a cleaned ITO substrate under the conditions of 1,500 rpm and 20 seconds, to form an organic layer having a thickness of 110 nm. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.15, 0.10) at the maximum luminance of 1,900 cd/m².

Example 7

N,N'-diphenyl-N,N'-di(α-naphthyl)benzidine (α-NPD) was vapor-deposited in a thickness of 40 nm on a cleaned ITO substrate placed in a deposition apparatus. Compound (1-15) was vapor-deposited in a thickness of 20 nm thereon, and the azole compound (Compound c) was then vapor-deposited in a thickness of 40 nm thereon. With a mask patterned for a desired light-emitting area of 4 mm×5 mm disposed on the resultant organic thin film, magnesium and silver were co-deposited at a mass ratio of magnesium/silver of 10:1 in a thickness of 50 nm on the organic thin film in the deposition apparatus, and silver was further vapor-deposited in a thickness of 50 nm thereon, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.08) at the maximum luminance of 3,200 cd/m². The external quantum efficiency of this light-emitting device was $\phi_{EL}$=1.2% in a calculated value. After leaving this light-emitting device in a nitrogen atmosphere for one day, the layer surface of the light-emitting device looked transparent.

Example 8

N,N'-diphenyl-N,N'-di(α-naphthyl)benzidine (α-NPD) was vapor-deposited in a thickness of 40 nm on a cleaned ITO substrate placed in a deposition apparatus. Compound (1-2) was vapor-deposited in a thickness of 20 nm thereon, and the azole compound (Compound c) was vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.08) at the maximum luminance of 1,400 cd/m². The external quantum efficiency of this light-emitting device was $\phi_{EL}$=1.5% in a calculated value. After leaving this light-emitting device in a nitrogen atmosphere for one day, the layer surface of the light-emitting device looked transparent.

Example 9

N,N'-diphenyl-N,N'-di(α-naphthyl)benzidine (α-NPD) was vapor-deposited in a thickness of 40 nm on a cleaned ITO substrate placed in a deposition apparatus. Compound (1-47) was vapor-deposited in a thickness of 20 nm thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.17, 0.17) at the maximum luminance of 6,470 cd/m². The external quantum efficiency of this light-emitting device was $\phi_{EL}$=3.4% in a calculated value. After leaving this light-emitting device in a nitrogen atmosphere for one day, the layer surface of the light-emitting device looked transparent.

Example 10

N,N'-diphenyl-N,N'-di(α-naphthyl)benzidine (α-NPD) was vapor-deposited in a thickness of 40 nm on a cleaned ITO substrate placed in a deposition apparatus. Compound (1-14) was vapor-deposited in a thickness of 20 nm thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.17) at the maximum luminance of 2,500 cd/m². The external quantum efficiency of this light-emitting device was $\phi_{EL}$=0.8% in a calculated value. After leaving this light-emitting device in a nitrogen atmosphere for one day, the layer surface of the light-emitting device looked transparent.

Example 11

N,N'-diphenyl-N,N'-di(α-naphthyl)benzidine (α-NPD) was vapor-deposited in a thickness of 40 nm on a cleaned ITO substrate placed in a deposition apparatus. Compound (1-1) was vapor-deposited in a thickness of 20 nm thereon, and Compound d was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 1,100 cd/m$^2$.

Example 12

N,N'-diphenyl-N,N'-di(α-naphthyl)benzidine (α-NPD) was vapor-deposited in a thickness of 40 nm on a cleaned ITO substrate placed in a deposition apparatus. Compound (1-47) was vapor-deposited in a thickness of 20 nm thereon, and Compound e was further vapor-deposited in a thickness of 40 nm thereon. A negative electrode was vapor-deposited on the resultant organic thin film in the same manner as in Comparative Example 1, to produce a light-emitting device. With a voltage of 9 V applied, the light-emitting device emitted blue light of 1,300 cd/m$^2$.

Example 13

N,N'-diphenyl-N,N'-di(α-naphthyl)benzidine (α-NPD) was vapor-deposited in a thickness of 40 nm on a cleaned ITO substrate placed in a deposition apparatus. Compound (1-47) was vapor-deposited in a thickness of 20 nm thereon, and Compound f was vapor-deposited in a thickness of 40 nm thereon. A negative electrode was vapor-deposited on the resultant organic thin film in the same manner as in Comparative Example 1, to produce a light-emitting device. With a voltage of 9 V applied, the light-emitting device emitted blue light of 1,200 cd/m$^2$.

Example 14

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound g were co-deposited in a thickness of 20 nm at a mass ratio of Compound (1-1)/Compound g of 100:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted orange light of 2,500 cd/m$^2$.

Example 15

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound h were co-deposited in a thickness of 20 nm at a mass ratio of Compound (1-1)/Compound h of 100:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted red light of 1,800 cd/m$^2$.

Example 16

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound i were co-deposited in a thickness of 20 nm at a mass ratio of Compound (1-1)/Compound i of 100:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted green light of 6,300 cd/m$^2$.

Example 17

N,N'-diphenyl-N,N'-di(α-naphthyl)benzidine (α-NPD) was vapor-deposited in a thickness of 40 nm on a cleaned ITO substrate placed in a deposition apparatus. Compound (1-2) and Compound j were co-deposited in a thickness of 20 nm at a mass ratio of Compound (1-2)/Compound j of 100:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted yellow green light of 4,500 cd/m$^2$.

Example 18

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound k were co-deposited in a thickness of 20 nm at a mass ratio of Compound (1-47)/Compound k of 100:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted yellow light of 3,900 cd/m$^2$.

Example 19

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound m were co-deposited in a thickness of 20 nm at a mass ratio of Compound (1-1)/Compound m of 10:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 2,800 cd/m$^2$.

Example 20

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound m were co-deposited in a thickness of 20 nm at a mass ratio of Compound (1-47)/Compound m of 1:10 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted bluish green light of 3,400 cd/m².

Example 21

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound n were co-deposited in a thickness of 20 nm at a mass ratio of Compound (1-1)/Compound n of 1:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 1,100 cd/m².

Example 22

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound o were co-deposited in a thickness of 20 nm at a mass ratio of Compound (1-1)/Compound o of 10:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 1,800 cd/m².

Example 23

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound p were co-deposited in a thickness of 20 nm at a mass ratio of Compound (1-1)/Compound p of 20:1 thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 3,800 cd/m².

Example 24

Compound q was vapor-deposited in a thickness of 40 nm on a cleaned ITO substrate placed in a deposition apparatus. Compound (1-1) was vapor-deposited in a thickness of 20 nm thereon, and Compound c was further vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 2,100 cd/m².

Example 25

Compound r was vapor-deposited in a thickness of 10 nm on a cleaned ITO substrate placed in a deposition apparatus. N,N'-diphenyl-N,N'-di(α-naphthyl)benzidine (α-NPD) was vapor-deposited in a thickness of 30 nm thereon, and Compound (1-1) was then vapor-deposited in a thickness of 20 nm thereon. Compound c was further vapor-deposited in a thickness of 40 nm thereon. A negative electrode was vapor-deposited on the resultant organic thin film in the same manner as in Comparative Example 1, to produce a light-emitting device. With a voltage of 6 V applied, the light-emitting device emitted blue light of 2,200 cd/m².

Example 26

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound (1-2) were co-deposited in a thickness of 20 nm at a mass ratio of Compound (1-1)/Compound (1-2) of 1:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 2,200 cd/m².

Example 27

N,N'-diphenyl-N,N'-di(α-naphthyl)benzidine (α-NPD) was vapor-deposited in a thickness of 40 nm on a cleaned ITO substrate placed in a deposition apparatus. Compound d and Compound k were co-deposited in a thickness of 5 nm at a mass ratio of Compound d/Compound k of 100:1 thereon, and Compound (1-1) and Compound p were then co-deposited in a thickness of 20 nm at a mass ratio of Compound (1-1)/Compound p of 20:1 thereon. Compound c was further vapor-deposited in a thickness of 20 nm thereon. A negative electrode was vapor-deposited on the resultant organic thin film in the same manner as in Comparative Example 1, to produce a light-emitting device. With a voltage of 8 V applied, the light-emitting device emitted white light of 4,100 cd/m².

Example 28

N,N'-diphenyl-N,N'-di(α-naphthyl)benzidine (α-NPD) was vapor-deposited in a thickness of 40 nm on a cleaned ITO substrate placed in a deposition apparatus. Compound (1-14) and Compound p were co-deposited in a thickness of 20 nm at a mass ratio of Compound (1-14)/Compound p of 20:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 2,900 cd/m².

Example 29

N,N'-diphenyl-N,N'-di(α-naphthyl)benzidine (α-NPD) was vapor-deposited in a thickness of 40 nm on a cleaned ITO substrate placed in a deposition apparatus. Compound (1-14) and Compound m were co-deposited in a thickness of 20 nm at a mass ratio of Compound (1-14)/Compound m of 1:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted blue light of 3,700 cd/m².

Example 30

N,N'-diphenyl-N,N'-di(α-naphthyl)benzidine (α-NPD) was vapor-deposited in a thickness of 40 nm on a cleaned ITO substrate placed in a deposition apparatus. Compound (1-1), Compound p and Compound g were co-deposited in a thickness of 20 nm at a mass ratio of Compound (1-1)/Compound p/Compound g of 100:5:0.2 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted white light of 1,800 cd/m².

Example 31

A cleaned ITO substrate was spin-coated with "Baytron P" (solution of PEDOT-PSS, poly(ethylenedioxythiophene) doped with polystyrene sulfonic acid, available from BAYER AG.) under the conditions of 1,000 rpm and 30 seconds, and vacuum-dried at 150° C. for 1.5 hours, to form an organic layer having a thickness of 70 nm. An organic layer thus obtained was spin-coated with a mixture of 10 mg of polymethyl methacrylate and 30 mg of Compound (1-1) in 4 ml of dichloroethane under the conditions of 1,500 rpm and 20 seconds, to form an organic layer having a total thickness of 120 nm Compound c was vapor-deposited in a thickness of 50 nm thereon. A negative electrode was vapor-deposited on the resultant organic thin film in the same manner as in Comparative Example 1, to produce a light-emitting device. With a voltage of 10 V applied, the light-emitting device emitted blue light of 800 cd/m².

Example 32

N,N'-diphenyl-N,N'-di(α-naphthyl)benzidine (α-NPD) was vapor-deposited in a thickness of 40 nm on a cleaned ITO substrate placed in a deposition apparatus. Compound (1-1) was vapor-deposited in a thickness of 20 nm thereon, and Compound d was then vapor-deposited in a thickness of 40 nm thereon. LiF was vapor-deposited in a thickness of 3 nm on the resultant organic thin film, and aluminum was then vapor-deposited in a thickness of 100 nm, to produce a light-emitting device. With a voltage of 8 V applied, the light-emitting device emitted blue light of 1,300 cd/m².

Example 33

N,N'-diphenyl-N,N'-di(α-naphthyl)benzidine (α-NPD) was vapor-deposited in a thickness of 40 nm on a cleaned ITO substrate placed in a deposition apparatus. Compound (1-2) and Compound s were co-deposited in a thickness of 20 nm at a mass ratio of Compound (1-2)/Compound s of 100:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted green light of 2,500 cd/m².

Example 34

N,N'-diphenyl-N,N'-di(α-naphthyl)benzidine (α-NPD) was vapor-deposited in a thickness of 40 nm on a cleaned ITO substrate placed in a deposition apparatus. Compound (1-2) and Compound t were co-deposited in a thickness of 20 nm at a mass ratio of Compound (1-2)/Compound t of 1:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted blue light of 1,500 cd/m².

Example 35

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound u were co-deposited in a thickness of 20 nm at a mass ratio of Compound (1-47)/Compound u of 100:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted green light of 2,700 cd/m².

Example 36

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound v were co-deposited in a thickness of 20 nm at a mass ratio of Compound (1-47)/Compound v of 100:1 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 8 V applied, the light-emitting device emitted reddish orange light of 2,200 cd/m².

Example 37

N,N'-diphenyl-N,N'-di(α-naphthyl)benzidine (α-NPD) was vapor-deposited in a thickness of 40 nm on a cleaned ITO substrate placed in a deposition apparatus. Compound (1-61) and Compound p were co-deposited in a thickness of 20 nm at a mass ratio of Compound (1-61)/Compound p of 100:2 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted blue light of 1,000 cd/m².

Example 38

N,N'-diphenyl-N,N'-di(α-naphthyl)benzidine (α-NPD) was vapor-deposited in a thickness of 40 nm on a cleaned ITO substrate placed in a deposition apparatus. Compound (1-65) and Compound s were co-deposited in a thickness of 20 nm at a mass ratio of Compound (1-65)/Compound s of 100:2 thereon, and Compound c was then vapor-deposited in a thickness of 40 nm thereon. A negative electrode was vapor-deposited on the resultant organic thin film in the same manner as in Comparative Example 1, to produce a light-emitting device. With a voltage of 7 V applied, the light-emitting device emitted blue light of 1,100 cd/m².

Example 39

N,N'-diphenyl-N,Nα-di(α-naphthyl)benzidine (α-NPD) was vapor-deposited in a thickness of 40 nm on a cleaned ITO substrate placed in a deposition apparatus. Compound (1-2) and Compound p were co-deposited in a thickness of 20 nm at a mass ratio of Compound (1-2)/Compound p of 95:5 thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.18) at the maximum luminance of 17,000 cd/m². The external quantum efficiency of this light-emitting device was $\phi_{EL}$=4% in a calculated value. After leaving this light-emitting device in a nitrogen atmosphere for one day, the layer surface of the light-emitting device looked transparent.

Example 40

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound p were co-deposited in a thickness of 20 nm at a mass ratio of Compound (1-47)/Compound p of 95:5 thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.20) at the maximum luminance of 10,000 cd/m². The external quantum efficiency of this light-emitting device was $\phi_{EL}$=3.5% in a calculated value. After leaving this light-emitting device in a nitrogen atmosphere for one day, the layer surface of the light-emitting device looked transparent.

Example 41

N,N'-diphenyl-N,N'-di(α-naphthyl)benzidine (α-NPD) was vapor-deposited in a thickness of 40 nm on a cleaned ITO substrate placed in a deposition apparatus. Compound (1-47) and Compound p were co-deposited in a thickness of 20 nm at a mass ratio of Compound (1-47)/Compound p of 99:1 thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.16, 0.18) at the maximum luminance of 12,000 cd/m². The external quantum efficiency of this light-emitting device was $\phi_{EL}$=3.5% in a calculated value. After leaving this light-emitting device in a nitrogen atmosphere for one day, the layer surface of the light-emitting device looked transparent.

Example 42

N,N'-diphenyl-N,N'-di(α-naphthyl)benzidine (α-NPD) was vapor-deposited in a thickness of 40 nm on a cleaned ITO substrate placed in a deposition apparatus. Compound (1-1) and Compound p were co-deposited in a thickness of 20 nm at a mass ratio of Compound (1-1)/Compound p of 95:5 thereon, and the azole compound (Compound c) was then vapor-deposited in a thickness of 40 nm thereon. A negative electrode was vapor-deposited on the resultant organic thin film in the same manner as in Comparative Example 1, to produce a light-emitting device. With respect to the light emitted from this light-emitting device, luminance and emission wavelength were measured in the same manner as in Comparative Example 1. As a result, it was found that the light-emitting device emitted blue light with a chromaticity of (0.15, 0.22) at the maximum luminance of 13,000 cd/m². The external quantum efficiency of this light-emitting device was $\phi_{EL}$=3.3% in a calculated value. After leaving this light-emitting device in a nitrogen atmosphere for one day, the layer surface of the light-emitting device looked transparent.

APPLICABILITY IN INDUSTRY

As described above in detail, the light-emitting device of the present invention exhibits excellent light-emitting efficiency, light-emitting properties, durability, heat resistance and amorphousness with less likelihood of being crystallized. The light-emitting device of the present invention having such characteristics can be used as a blue light-emitting device or a white light-emitting device with high color purity useful for indicating elements, displays, backlights, electrophotography, illumination light sources, recording light sources, exposing light sources, reading light sources, signs and marks, signboards, interiors, optical communications devices, etc. The compound (1) used in the light-emitting device of the present invention can be used as a material for organic EL devices, and be further applied to medical applications, fluorescent-whitening agents, materials for photography, UV-absorbing materials, laser dyes, dyes for color filters, color conversion filters, organic semiconductor materials, electrically conductive organic materials, etc.

What is claimed is:
1. A light-emitting device comprising a pair of electrodes and a light-emitting layer or a plurality of organic layers comprising a light-emitting layer disposed between said electrodes, said light-emitting layer or at least one of a plurality of organic layers comprising said light-emitting layer comprising at least one compound represented by the following general formula (6):

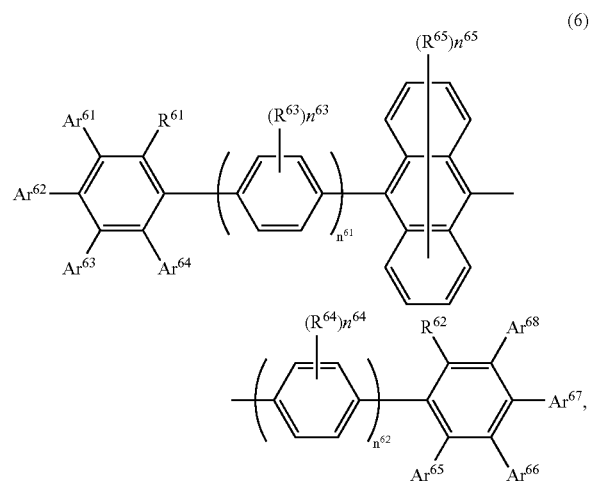

wherein each of $Ar^{61}$, $Ar^{62}$, $Ar^{63}$, $Ar^{64}$, $Ar^{65}$, $Ar^{66}$, $Ar^{67}$ and $Ar^{68}$ is selected from the group consisting of a phenyl group, a napthyl group and a phenanthryl group; $Ar^{61}$, $Ar^{62}$, $Ar^{63}$ and $Ar^{64}$ are not bonded to each other to form a ring and $Ar^{65}$, $Ar^{66}$, $Ar^{67}$ and $Ar^{68}$ are not bonded to each other to form a ring; each of $R^{61}$ and $R^{62}$ represents a hydrogen atom or a substituent; each of $n^{61}$ and $n^{62}$ represents and integer of 0 to 5; each of $n^{63}$ and $n^{64}$ represents 0; and $n^{65}$ represents 0.

2. The light-emitting device of claim 1, wherein in said general formula (6), each of $R^{61}$ and $R^{62}$ is selected from the group consisting of a hydrogen atom, a phenyl group and a pyrenyl group.

3. The light-emitting device of claim 1, wherein in said general formula (6), each of $n^{61}$ and $n^{62}$ represents 0 or 1.

4. The light-emitting device of claim 1, wherein in said general formula (6), each of $n^{61}$ and $n^{62}$ represents 0.

5. The light-emitting device of claim 1, wherein in said general formula (6), each of $Ar^{61}$, $Ar^{62}$, $Ar^{63}$, $Ar^{64}$, $Ar^{65}$, $Ar^{66}$, $Ar^{67}$ and $Ar^{68}$ represents a phenyl group.

* * * * *